(12) United States Patent
Holmes et al.

(10) Patent No.: US 12,243,014 B2
(45) Date of Patent: Mar. 4, 2025

(54) NETWORK-ENABLED GLOBAL POSITIONING SATELLITE-BASED DEVICE FOR OBTAINING PATIENT VERIFICATION

(71) Applicant: Rearden Analytics, Brentwood, TN (US)

(72) Inventors: Larry Leighton Holmes, Fairhope, AL (US); Eric Jason Shiflet, Franklin, TN (US); William Stephen McConnell, IV, Brentwood, TN (US); Auston Guillium DeVille, Huntingdon, TN (US)

(73) Assignee: Rearden Analytics, Brentwood, TN (US)

( * ) Notice: Subject to any disclaimer, the term of this patent is extended or adjusted under 35 U.S.C. 154(b) by 127 days.

(21) Appl. No.: 17/081,127

(22) Filed: Oct. 27, 2020

(65) Prior Publication Data
US 2021/0042704 A1 Feb. 11, 2021

(51) Int. Cl.
*G06Q 10/10* (2023.01)
*G16H 10/60* (2018.01)
(Continued)

(52) U.S. Cl.
CPC ............. *G06Q 10/10* (2013.01); *G16H 10/60* (2018.01); *G16H 40/40* (2018.01); *G16H 40/60* (2018.01)

(58) Field of Classification Search
None
See application file for complete search history.

(56) References Cited

U.S. PATENT DOCUMENTS 7,421,399 B2   9/2008   Kimmel
7,979,286 B2   7/2011   Manning et al.
(Continued)

OTHER PUBLICATIONS

Tzavaras et al. "Development of a system for telemonitoring of respiration parameters for patients with Obstructive Sleep Apnea " 2014 36th Annual International Conference of the IEEE Engineering in Medicine and Biology Society, Chicago, IL, USA, 2014, pp. 3472-3475, doi: 10.1109/EMBC.2014.6944370. (Year: 2014).*

*Primary Examiner* — Jonathan Ng
(74) *Attorney, Agent, or Firm* — Hoffmann & Baron, LLP

(57) ABSTRACT

A patient treatment system includes a communications module coupled to a communication network, an agreement signification device for capturing data indicative of a signature of a patient, a sensor for monitoring parameters associated with medical equipment prescribed for treatment of the patient, and a microcontroller coupled with the communications module and the sensor. The microcontroller is configured: to obtain information associated with the patient, the medical equipment, a physician and/or an ancillary provider, the information including an agreement by the patient verifying the accuracy of data entered into the patient treatment system; to convert the information into a digital format enabling verification that the information complies with prescribed treatment associated with the medical equipment; to transmit data indicative of real-time status and usage of the medical equipment; and to generate a signal causing the medical equipment to automatically administer or discontinue administration of the prescribed treatment using the medical equipment.

18 Claims, 7 Drawing Sheets

(51) Int. Cl.
*G16H 40/40* (2018.01)
*G16H 40/60* (2018.01)

(56) References Cited

U.S. PATENT DOCUMENTS

| | | | |
|---|---|---|---|
| 2002/0082480 A1* | 6/2002 | Riff | G16H 40/67 |
| | | | 600/300 |
| 2002/0133376 A1* | 9/2002 | Fritschen | H04N 1/32101 |
| | | | 705/2 |
| 2003/0163350 A1 | 8/2003 | Rudowski et al. | |
| 2003/0171950 A1 | 9/2003 | Kilgannon et al. | |
| 2004/0172301 A1* | 9/2004 | Mihai | A61B 5/0002 |
| | | | 705/2 |
| 2006/0167509 A1* | 7/2006 | Boute | A61N 1/3627 |
| | | | 607/9 |
| 2007/0032733 A1* | 2/2007 | Burton | A61B 5/7264 |
| | | | 600/509 |
| 2007/0299776 A1 | 12/2007 | Frustaci et al. | |
| 2008/0033304 A1* | 2/2008 | Dalal | A61B 5/4812 |
| | | | 600/529 |
| 2008/0091468 A1* | 4/2008 | Heidenreich | G16H 80/00 |
| | | | 705/3 |
| 2008/0133274 A1 | 6/2008 | Warner | |
| 2008/0244721 A1 | 10/2008 | Barrus et al. | |
| 2009/0099876 A1 | 4/2009 | Whitman | |
| 2009/0107498 A1* | 4/2009 | Plattner | A61M 16/0051 |
| | | | 128/204.23 |
| 2009/0204434 A1* | 8/2009 | Breazeale, Jr. | H04L 12/1886 |
| | | | 705/2 |
| 2009/0259491 A1 | 10/2009 | Busch | |
| 2010/0079242 A1 | 4/2010 | Martis et al. | |
| 2010/0185463 A1 | 7/2010 | Noland et al. | |
| 2010/0312575 A1* | 12/2010 | Witt | G16H 40/40 |
| | | | 705/2 |
| 2010/0332252 A1 | 12/2010 | Beraja et al. | |
| 2011/0077967 A1 | 3/2011 | Kapu et al. | |
| 2011/0112857 A1 | 5/2011 | Yurko et al. | |
| 2011/0258004 A1 | 10/2011 | Dean et al. | |
| 2012/0109829 A1 | 5/2012 | McNeal et al. | |
| 2012/0182143 A1 | 7/2012 | Gaines et al. | |
| 2012/0191485 A1 | 7/2012 | Boyer et al. | |
| 2012/0203566 A1 | 8/2012 | Kidd et al. | |
| 2013/0060576 A1 | 3/2013 | Hamm et al. | |
| 2013/0087609 A1 | 4/2013 | Nichol et al. | |
| 2013/0197923 A1* | 8/2013 | Hill | G06Q 30/04 |
| | | | 705/2 |
| 2014/0052466 A1* | 2/2014 | DeVille | G16H 10/60 |
| | | | 705/2 |
| 2015/0057634 A1* | 2/2015 | Mastrototaro | G16H 20/17 |
| | | | 604/151 |

\* cited by examiner

NETWORK-ENABLED GLOBAL POSITIONING SATELLITE-BASED DEVICE FOR OBTAINING PATIENT VERIFICATION

BACKGROUND

Embodiments disclosed herein are directed to a network-enabled global positioning satellite-based device that obtains patient verification of information in the medical field and, more particularly, to such devices and methods for use in the provision and maintenance of durable medical equipment.

Difficulties in providing durable medical equipment are widespread. For example, the Department of Health and Human Services/Office of Inspector General (HHS/OIG) found that an estimated 61 percent of power wheelchairs provided to Medicare beneficiaries in the first half of 2007 were medically unnecessary or had claims that lacked sufficient documentation to determine medical necessity. The estimate was based on records submitted by suppliers that provided the power wheelchairs. HHS/OIG recommended that Medicare enhance reenrollment screening standards for current DME suppliers, review records from sources in addition to the supplier, such us the prescribing physician, to determine medical necessity, continue supplier and physician education, and review the suppliers of the sampled claims found to be in error.

HHS calculated and reported in its FY 2011 Agency Financial Report the three-year weighted average national Medicaid error rate that includes rates from fiscal years 2009, 2010, and 2011. This three-year rolling national error rate is 8.1 percent or $21.9 billion in estimated improper payments, which represents a reduction from FY 2010 (9.4 percent). The weighted national error component rates are as follows: Medicaid FFS, 2.7 percent; Medicaid managed care, 0.3 percent; and Medicaid eligibility, 6.1 percent. The most common cause of errors in fee-for-service claims is the lack of sufficient documentation to support payments. Medicare does not require durable medical equipment (DME) ancillary provider companies to prove that they have the required documentation before the DME is provided. The vast majority of eligibility errors were due to beneficiaries found to be ineligible or whose eligibility status could not be determined. The reports of fraudulent activity provided above were obtained from a document entitled "The Department of Health and Human Services and The Department of Justice Health Care Fraud and Abuse Program Annual Report for Fiscal Year 2011" (http://oig.hhs.gov/publications/docs/hcfac/hcfacreport2011.pdf).

Currently, there are no devices, methods, or systems to address these issues in an effective manner. Therefore, there is a substantial need to reduce errors that remain prevalent in the provision of durable medical equipment to patients that desperately need these devices.

SUMMARY

In accordance with one embodiment of the disclosed subject matter, a patient treatment system includes a network server, an agreement signification device, a global positioning system device, a network-enabled sensor, and a computer readable medium including instructions that, when executed by the network server, perform operations. These operations include obtaining, using the agreement signification device, global positioning system device, and network-enabled sensor, information that is input into the network server and is associated with at least one of a patient, medical equipment, a physician, and an ancillary provider. The information includes a signature of the patient representing agreement of the patient with data entered by the physician including (1) whether the patient is benefitting from use of the medical equipment, (2) whether the patient needs to continue use of the medical equipment, and (3) hours of operation of the medical equipment. The operations include coupling the medical equipment to the network-enabled sensor. The network-enabled sensor transmits at least one of airflow into the medical equipment, airflow out of the medical equipment, and electronic current rating associated with the medical equipment to the network server. The information that is input into the patient treatment system includes at least one of airflow into the medical equipment, airflow out of the medical equipment, and electronic current rating associated with the medical equipment. The operations include converting the information into a digital format enabling verification that the information complies with treatment associated with the medical equipment. The operations include providing, using a client user computer, selective real-time access to the information, wherein the access is selectively provided in real-time to at least one of the physician, ancillary provider, a payor, and an auditor. The operations include delivering or discontinuing administration of at least one of airway pressure, air, oxygen, transcutaneous electrical nerve stimulation, continuous passive motion, mobility assistance, parenteral nutrition, enteral nutrition, and dialysis to the patient, using the medical equipment, based on the information by providing a command to at least one of the physician and ancillary provider using the client user computer communicatively coupled to the network server computer, the medical equipment including at least one of an airway pressure device, ventilator, oxygen delivery device, parenteral nutrition device, enteral nutrition device, and dialysis device.

In accordance with another embodiment of the disclosed subject matter, a patient treatment system includes a network server, an agreement signification device, a global positioning system device, a network-enabled sensor, and a computer readable medium including instructions that, when executed by the network server computer, perform operations. The operations include obtaining, using the agreement signification device, global positioning system device, and network-enabled sensor, information that is input into the network server computer and is associated with at least one of a patient, the medical equipment, a physician, and an ancillary provider. The information includes the patient's signature representing agreement of the patient with data entered by the physician comprising at least one of (1) whether the patient is benefitting from use of the medical equipment, (2) whether the patient needs to continue use of the medical equipment, and (3) hours of operation of the medical equipment. The operations include coupling the medical equipment to the network-enabled sensor, wherein the network-enabled sensor transmits at least one of airflow into the medical equipment, airflow out of the medical equipment, and electronic current rating associated with the medical equipment to the network server. The information that is input into the patient treatment system includes at least one of airflow into the medical equipment, airflow out of the medical equipment, and electronic current rating associated with the medical equipment. The operations include converting the information into a digital format enabling verification that the information complies with treatment associated with the medical equipment. The operations include providing, using a client user computer, selective real-time access to the information, wherein the access is selectively provided in real-time to at least one of the physician, ancillary provider, a payor, and an auditor. The operations include delivering treatment to the patient or removing treatment from the patient, using the medical equipment, based on the information by providing a command to at least one of the physician and ancillary provider using the client user computer communicatively coupled to the network server computer. The medical equipment includes at least one of an airway pressure device, ventilator, oxygen delivery device, parenteral nutrition device, enteral nutrition device, and dialysis device.

In accordance with another embodiment of the disclosed subject matter, a patient treatment system includes a network server, an agreement signification device, a network-enabled sensor, and a computer readable medium including instructions that, when executed by the network server computer, perform operations including obtaining, using the agreement signification device and network-enabled sensor, information that is input into the network server computer and is associated with at least one of a patient, the medical equipment, a physician, and an ancillary provider, wherein the information includes the patient's signature representing agreement of the patient with data entered by the physician comprising at least one of (1) whether the patient is benefitting from use of the medical equipment, (2) whether the patient needs to continue use of the medical equipment, and (3) hours of operation of the medical equipment. The operations include coupling the medical equipment to the network-enabled sensor, wherein the network-enabled sensor transmits at least one of airflow into the medical equipment, airflow out of the medical equipment, and electronic current rating associated with the medical equipment to the network server. The information that is input into the patient treatment system includes at least one of airflow into the medical equipment, airflow out of the medical equipment, and electronic current rating associated with the medical equipment. The operations include converting the information into a digital format enabling verification that the information complies with treatment associated with the medical equipment. The operations include providing, using a client user computer, selective real-time access to the information, wherein the access is selectively provided in real-time to at least one of the physician, ancillary provider, a payor, and an auditor. The operations include delivering the medical equipment to the patient or removing the medical equipment from the patient based on the information by providing a command to at least one of the physician and ancillary provider using the client user computer communicatively coupled to the network server computer. The medical equipment includes at least one of an airway pressure device, ventilator, oxygen delivery device, parenteral nutrition device, enteral nutrition device, and dialysis device.

In accordance with another embodiment of the disclosed subject matter, a patient treatment system includes a network server, an agreement signification device, a network-enabled sensor, and a computer readable medium including instructions that, when executed by the network server computer, perform operations including obtaining, using the agreement signification device and network-enabled sensor, information that is input into the network server computer and is associated with at least one of a patient, the medical equipment, a physician, and an ancillary provider. The information includes the patient's signature representing agreement of the patient with data entered by the physician comprising at least one of (1) whether the patient is benefitting from use of the medical equipment, (2) whether the patient needs to continue use of the medical equipment, and (3) hours of operation of the medical equipment. The operations include coupling the medical equipment to the network-enabled sensor, wherein the network-enabled sensor transmits at least one of airflow into the medical equipment, airflow out of the medical equipment, and electronic current rating associated with the medical equipment to the network server. The information that is input into the patient treatment system includes at least one of airflow into the medical equipment, airflow out of the medical equipment, and electronic current rating associated with the medical equipment. The operations include converting the information into a digital format enabling verification that the information complies with treatment associated with the medical equipment. The operations include providing, using a client user computer, selective real-time access to the information, wherein the access is selectively provided in real-time to at least one of the physician, ancillary provider, a payor, and an auditor. The operations include delivering the medical equipment to the patient or removing the medical equipment from the patient based on the information by providing a command to at least one of the physician and ancillary provider using the client user computer communicatively coupled to the network server computer. The medical equipment includes in-home diagnostic testing and gathering equipment including at least one of a blood gasses device, international normalized ratio (INR) Coumadin® testing device, spirometry device, and pulse oximetry device.

Embodiments of the disclosed subject matter will become apparent from the following detailed description, which is to be read in connection with the accompanying drawings.

BRIEF DESCRIPTION OF THE DRAWINGS

The following drawings are presented by way of example only and without limitation, wherein like reference numerals, when used, indicate corresponding elements throughout the several views, and wherein.

Figure 1:
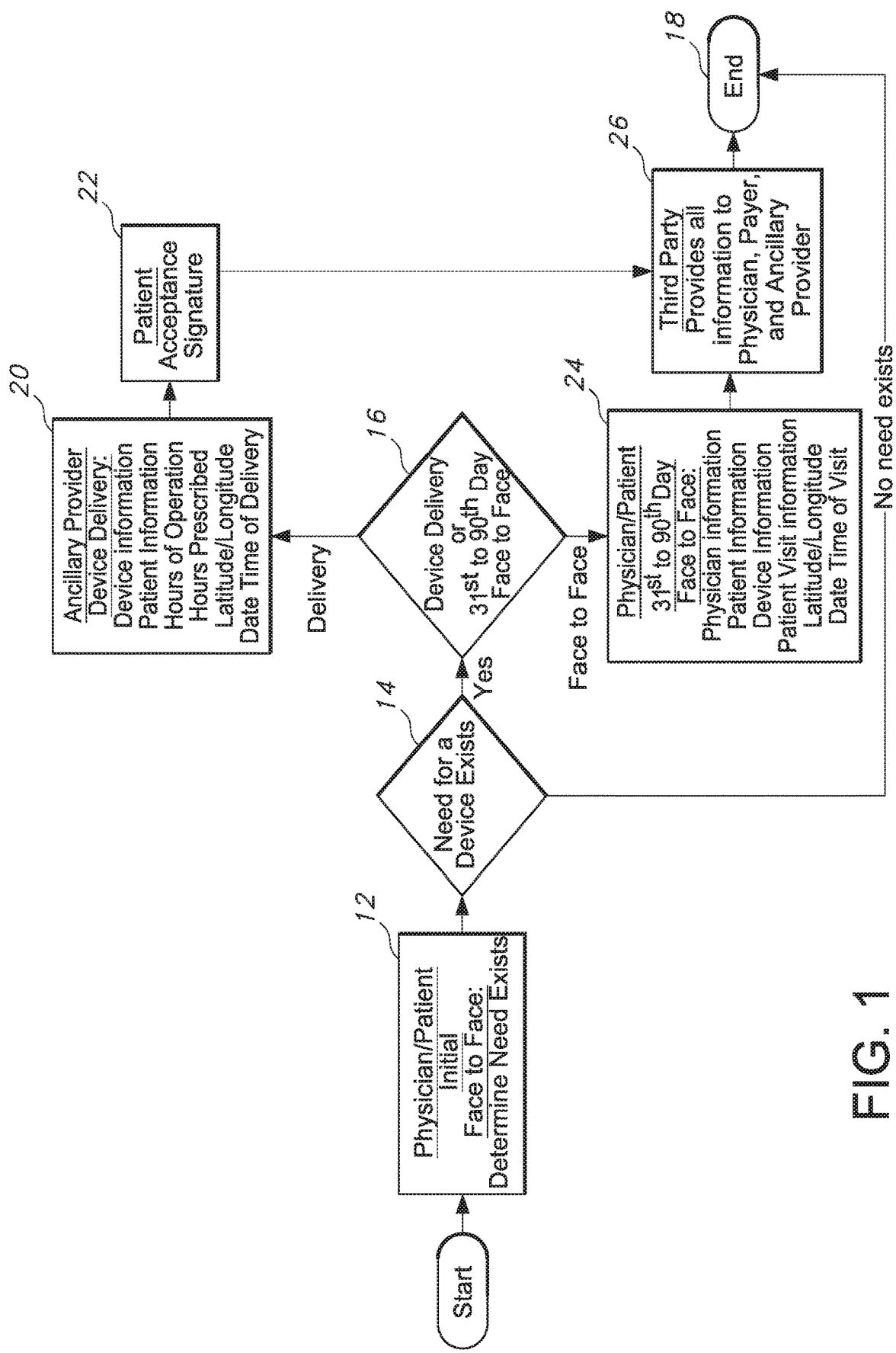
FIG. 1 is a flowchart of a third-party durable medical equipment (DME) provision process workflow.

It is to be appreciated that elements in the figures are illustrated for simplicity and clarity. Common but well-understood elements that are useful in a commercially feasible embodiment are not necessarily shown in order to facilitate a less hindered view of the illustrated embodiments.

DETAILED DESCRIPTION

Embodiments of the disclosed subject matter are directed to network-enabled devices and methods for obtaining patient verification to reduce errors associated with the provision and maintenance of durable medical equipment. The embodiments disclosed herein will be described in the context of devices, methods, systems, and computer-readable media that eliminate or substantially reduce the potential for mistakes and delays associated with the provision and maintenance of durable medical equipment when compared with conventional techniques for doing so, while reducing the amount of human intervention required to perform these techniques. It should be understood, however, that the embodiments herein are not limited to these or any other particular devices, methods, systems, and computer-readable media.

The disclosed embodiments provide a third-party operational tool for validating the provision of treatment using DME, decreasing paperwork, decreasing manual labor, and increasing accuracy. The tool utilizes 31 to 90-day face-to-face visits between the patient and physician, as well as capture of the patients' signature. The (1) latitude and longitude coordinates, (2) date and time stamps, and (3) user credentials or user signatory verification are captured each time data is acquired during the patient's journey through the DME provision process. The tool also makes data available to certified and approved parties within HIPAA guidelines, which can be made selective by utilizing different authorization levels for different parties. Therefore, the tool reduces errors that remain prevalent in the reimbursement process concerning durable medical equipment by providing proof that the required information exists before the DME is administered.

Embodiments provide for a third-party DME provision application, which is accomplished through a process that captures information between an ordering physician and a patient, and then provides the information to the patient's insurance company and ancillary provider. The application also captures global positioning system (GPS) location information upon each completion of the application to ensure that delivered durable medical equipment and physician visits are verifiable. In some embodiments, the physician or ancillary provider cannot alter the information without review and verification represented by the patients' signature.

The following list of terminology and their respective definitions are intended to provide guidance regarding the meaning of terms used herein without limitation thereto.

Ancillary Company or Provider (AC)—are companies or entities that provide services and products to physicians and patients. ACs often act as middle-men or intermediaries that obtain durable medical equipment (DME) from DME manufacturers, ship the DME to patients, and bill insurance companies, including Medicare and Medicaid, as well as private insurers, to obtain reimbursement for the DME.

Durable Medical Equipment (DME)—are products used by physicians and patients to treat illnesses such as, but not limited to mobility walkers, oxygen concentrators, lift chairs, continuous positive airway pressure (CPAP) systems, intermittent assist devices, airway pressure devices, ventilators, oxygen delivery devices, transcutaneous electrical nerve stimulation devices, prosthetic devices, orthotic devices, continuous passive motion devices, mobility assistance devices, parenteral nutrition devices, enteral nutrition devices, and dialysis devices. Durable Medical Equipment can also be referred to as "Home Medical Equipment (HME)" and also as "Durable Medical Equipment, Prosthetics, Orthotics, and Supplies (DMEPOS)" as set forth in greater detail by the Centers for Medicare and Medicaid Services at http://www.cms.gov/Regulations-and-Guidance/Guidance/Manuals/Downloads/clm104c20.pdf, the content of which is incorporated by reference herein. For the purposes of this document, all references to DME herein are intended to include any device that may be defined as home medical equipment (HME) or durable medical equipment, prosthetics, orthotics, supplies (DMEPOS).

Ancillary Company Technician (AC Technician)—delivers durable medical equipment (DME) to the patient, performs setup operations associated with the DME, provides instructions to the patient, and returns to the patient for follow-up inspections of the DME.

Continuous Positive Airway Pressure (CPAP) systems—use mild air pressure to keep airways open for the treatment of patients who have breathing problems. Face-to-Face (visit or encounter)—is an in person encounter between a patient and their medical provider. In some cases, this may also be performed with a telemedicine video conferencing system.

Electronic Medical Record (EMR)—is a computerized repository or database intended for storage, retrieval, and modification of patient medical records.

Progress Notes—are the part of a medical record where healthcare professionals record details to document a patient's clinical status or achievements during the course of a hospitalization or over the course of outpatient care Patient Journey—is a complete set of information starting from a first contact that a patient has with a medical provider through the patient's recovery.

Centers for Medicare and Medicaid Services (CMS)—previously known as the Health Care Financing Administration (HCFA), is a federal agency within the United States Department of Health and Human Services (DHHS) that administers the Medicare program and works in partnership with state governments to administer Medicaid, the State Children's Health Insurance Program (SCHIP), and health insurance portability standards.

Health Insurance Portability and Accountability Act (HIPAA)—is a U.S. law designed to provide privacy standards to protect patients' medical records and other health information provided to health plans, doctors, hospitals, and other health care providers. Developed by the Department of Health and Human Services, these new standards provide patients with access to their medical records and more control over how their personal health information is used and disclosed. They represent a uniform, federal floor of privacy protections for consumers across the country. State laws providing additional protections to consumers are not affected by this new rule. HIPAA took effect on Apr. 14, 2003.

Certified Audit Entity—includes a recovery audit contractor or anyone approved by at least the payor, physician, or AC to perform audits.

Recovery Audit Contractor (RAC)—is a person or entity enabled by the Tax Relief and Health Care Act of 2006 to identity improper Medicare payments in all 50 states. RACs are paid on a contingency fee basis, and receive a percentage of improper overpayments and underpayments that they collect from providers, as set forth in greater detail at http://www.aha.org/advocacy-issues/rac/index.shtml, the content of which is incorporated by reference herein.

Medicare Administration Contractors (MAC)—A company under contract with the federal government to handle claims processing for Medicare services.

Zone Program Integrity Contractors (ZPIC)—An entity established by the Centers for Medicare & Medicaid Services (CMS) to combat fraud, waste, and abuse in the Medicare program. As a result of the Medicare Prescription Drug, Improvement, and Modernization Act of 2003, which established 7 zones throughout the United States for the purpose of processing Medicare claims, CMS created ZPICs to more effectively protect the Medicare program. ZPICs replaced Program Safeguard Contractors (PSC), which had been established by the Health Insurance Portability and Accountability Act of 1996.

Office of Inspector General (OIG)—Since its 1976 establishment, the Office of Inspector General of the U.S. Department of Health & Human Services (HHS) has been at the forefront of the Nation's efforts to fight waste, fraud, and abuse in Medicare, Medicaid and more than 300 other HHS programs as set forth in greater detail at http://oig.hhs.gov, the content of which is incorporated by reference herein.

Health Care Fraud Prevention and Enforcement (HEAT)—on May 20, 2009, Attorney General Holder and Secretary Sebelius announced the Health Care Fraud Prevention & Enforcement Action Team, which is a new effort with increased tools, resources, and a sustained focus by senior level leadership to enhance collaboration between the Department of Health and Human Services (HHS) and the Department of Justice (DOJ). HEAT is committed to preventing and prosecuting health care fraud. HEAT is jointly led by the Deputy Attorney General and HHS Deputy Secretary, and includes top-level law enforcement agents, prosecutors, attorneys, auditors, evaluators, and other staff from the DOJ and HHS and their operation divisions, and is dedicated to joint efforts across governmental agencies to prevent fraud and enforce current anti-fraud laws around the country. Medicare Fraud Strike Force teams are a key component of HEAT, as described in greater detail at http://www.stopmedicarefraud.gov, the content of which is incorporated by reference herein.

Payer—includes both public and private insurance companies and entities.

Quick Response Code (QR Code) refers to a type of matrix bar code (or two-dimensional code) first designed for the automotive industry. More recently, the code has become popular beyond the automotive industry due to its readability and large storage capacity in comparison to standard universal product code (UPC) bar codes. QR code includes black modules, which appear as square dots, arranged in a square pattern on a white background. The encoded information can be made up of four standardized kinds or so-called "modes" of data, which include numeric, alphanumeric, byte/binary, and Kanji or, through supported extensions, virtually any kind of data, as is further described at http://en.wikipedia.org/wiki/QR_code, the content of which is incorporated by reference herein.

DataMatrix Code—is a two-dimensional matrix bar code, which includes black and white cells or modules arranged in either a square or rectangular pattern. The information to be encoded can be text or numeric data, as is further described at http://en.wikipedia.org/wiki/Data_Matrix, the content of which is incorporated by reference herein.

The workflow or process of the physician, patient, and AC encounter is described in relation to a workflow 10 shown in FIG. 1. Primary responsibility for blocks 12 and 24 is with the physician; primary responsibility for blocks 14, 16, and 26 is with a third-party; primary responsibility for block 20 is with the ancillary provider; and primary responsibility for block 22 is with the patient. First, the patient visits the physician for an initial face-to-face meeting or visit in step 12 to determine whether DME is or is not needed by the patient in step 14. If the physician determines that the patient needs DME to improve the patient's health, this process continues with step 16, and if the physician determines that the patient does not need DME to improve the patient's health, this process ends with step 18.

If the physician finds a need for DME, the AC receives a prescription for DME and supplies from the physician. For example, if the physician determines that a continuous positive airway pressure (CPAP) device is needed, a humidification device may also be necessary if the patient's nasal passages are drying. The AC contacts the patient and then delivers and sets up the DME in the patient's home or the patient acquires the DME at the ACs office or facility in step 20.

The AC acquires information concerning the DME setup, which includes a delivery ticket and documentation, and then provides this information to the physician. DME information acquired at this time includes, but is not limited to a manufacturer, make, model, serial number, lot number, quantity, full description, patient demographics, patient cost, including a patient signature 33 or electronic signature, and date, which is acquired in step 22. The AC technician leaves forms with the patient, such as, but not limited to, a patient's bill of rights, insurance documents, warrantee concerning the DME, and the like.

The physician completes any forms or questionnaires provided by the AC and then signs and dates these forms and returns these forms with progress notes from the initial face-to-face visit, a sleep study report from the physician's standard progress notes from the initial face-to-face visit prior to conducting the sleep study, and a polysinography sleep study to rule out obstructive sleep apnea (OSA). For example, if the patient exhibits an apnea hypopnea index of fifteen (15) or more events per hour or between five (5) and fourteen (14) events per hour with documented symptoms of daytime hypersomilance, which includes, for example, fatigue, moodiness, history of stroke, ischemic heart disease, and the like, then the patient qualifies for a CPAP and supplies. If this is the case, then for all follow-up visits between the 31st and 90th day following CPAP setup, the patient is required to be on the CPAP device a minimum of thirty (30) consecutive nights for at least four (4) hours per night with 70% compliance over that 30-day period. Such a patient must return to the treating physician for a follow-up face-to-face visit and that patient must state that he or she is improving from and must continue use of the DME. An improvement from the use of the DME is shown if the patient believes that he or she is feeling and sleeping better.

The Epworth sleepiness scale, which is used to determine the level of daytime sleepiness, provides another indication of improvement. For example, a score of 10 or more is considered sleepy, and will qualify a patient for a CPAP device. The physician or a sleep lab can determine the Epworth score.

The patient is required to have another face-to-face visit with the physician between the 31st and 90th day following receipt of the DME and required documentation from the AC technician in step 24. The physician determines whether the DME device is improving the patient's health. Determination of whether the patient is using the DME can be made by verifying the hours-of-operation displayed on the DME, if the DME is equipped with an hours-of-operation meter or a memory that actively stores a digital version of DME usage activity statistics. Whether the patient has had any problems with the DME can be determined by asking the patient. Whether the patient is benefitting from the DME can be determined by asking for the patient's opinion and/or a physical inspection of the patient by the physician.

Figure 2:
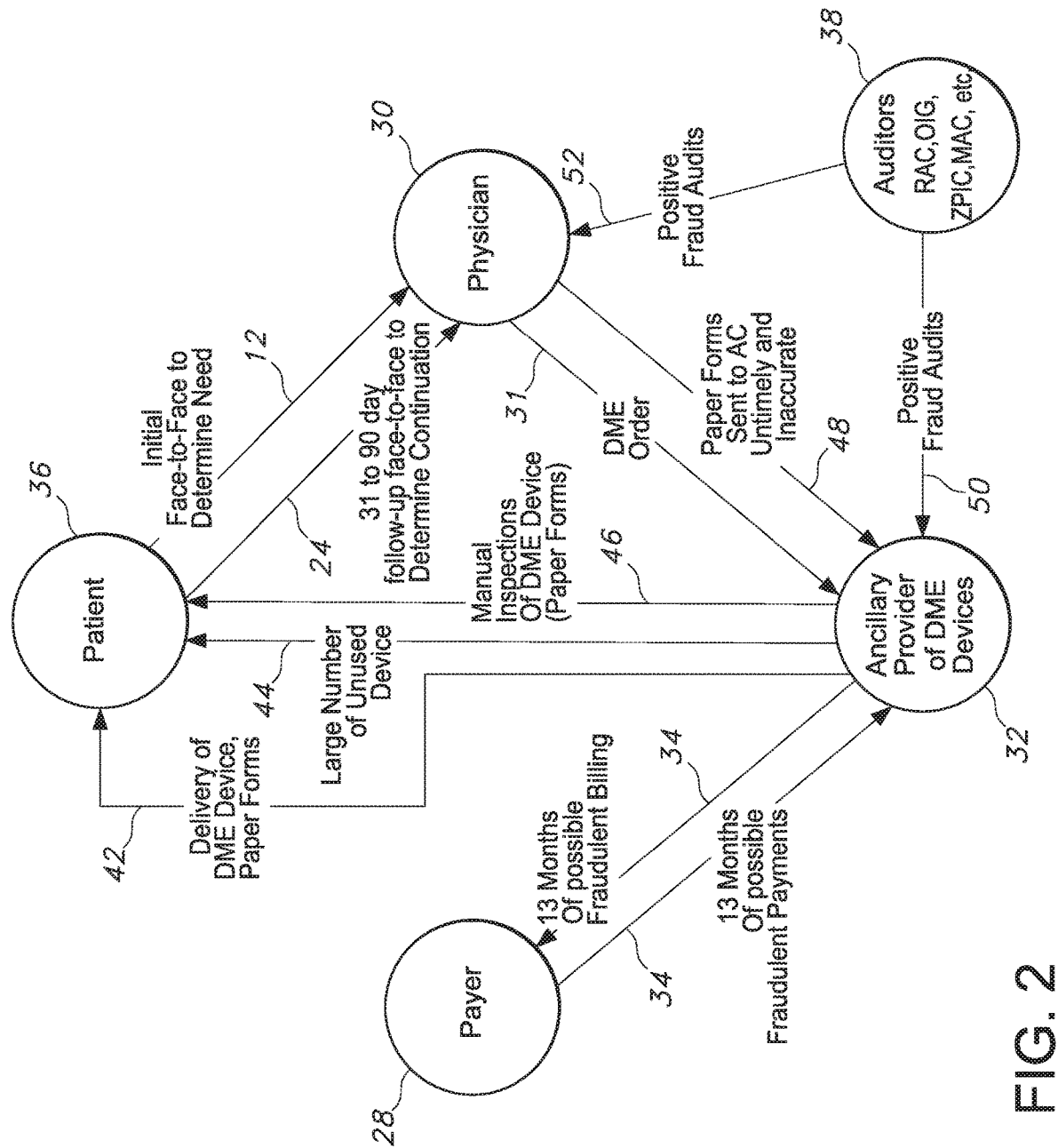
FIG. 2 is a relational diagram showing issues with the provision of durable medical equipment.

If the patient is not benefiting from the DME, the AC can then reacquire the DME from the patient and should stop billing the payer for the DME. If the patient is benefiting from the DME, the AC will continue billing for the DME for a total of thirteen (13) months following delivery of the DME. After thirteen (13) months following delivery of the DME, the patient owns the DME, which is one reason why the patient is provided with warrantee 42 concerning the DME upon delivery of the DME to the patient as shown in FIG. 2. The thirteen-month regulation provides a potential for thirteen (13) months of fraudulent billing 34 by the AC 32 and thirteen (13) months of fraudulent payment 34 by the payer 28.

The AC is required to warrantee the DME for a total of five (5) years from the date of delivery of the DME to the patient. If the DME is faulty, the AC must fix or replace the DME. Billing for the DME by the AC does not occur after thirteen (13) months following delivery of the DME to the patient. Medicare will pay for parts associated with the DME at a prevailing wholesale rate for the part and will pay at a rate of $11 per 15 minutes of labor.

ACs are required to keep all documentation for four (4) years for all preliminary audits. However, audits can go back seven (7) years, and thus records should be kept for at least seven (7) years. Pediatric patient documentation must be retained until the patient reaches twenty-five years of age or for the aforementioned 4-7 year time frames depending on which timeframe is longer. The third-party will maintain a record of all information obtained in steps 20, 22, and 24, and will make this information available to the physician, payer, and AC or ancillary provider in step 26.

The embodiments disclosed herein seek to address problems and issues, some of which are shown in FIG. 2. These problems are associated with public and private insurance companies and entities concerning the effective delivery of and treatment by durable medical equipment (DME), which include, but are not limited to, the following:

- payers 28, such as Medicare®, United Healthcare®, Cigna®, Blue Cross Blue Shield® and the like, do not see information relevant to the patient and DME throughout the patient, physician, ancillary company (AC) encounter during the lifecycle of the DME; the physician 30 and AC 32 control information relevant to the patient and DME, which enables negligent and/or intentional billing fraud 34;
- the payer 28 does not have a complete record of the patient's journey regarding the DME, which is necessary to comply with billing regulations and policies concerning the DME;
- the physician 30 does not have a complete record of the patient's journey regarding the DME, which is necessary to comply with billing regulations and policies concerning the DME.
- the physician 30 realizes substantial additional manual labor costs associated with completing, acquiring, and transferring additional documentation to and from the AC so that the patient can receive the DME, and so that the AC can be properly paid by the payer. Much of this additional documentation is required by the payer to prevent fraud. The cost of this additional manual labor can be as much as $10 to $30 for each patient visit.
- the patient 36 may not be using the DME as prescribed by the physician 30 even though the payer may still be paying bills that the AC 32 continues to submit concerning the DME.
- the AC 32 has a difficult time acquiring the documentation required by the payer 28 from the physician 30 in an accurate and timely manner to complete the billing process and obtain reimbursement from the payer 28;
- the AC 32 continues to bill for DME even though the AC 32 does not have all of the required documentation including patient records. Most of the documentation issues are due to an unresponsive physician 30 who simply does not return the patient 28 face-to-face visit information in an accurate and/or timely manner. The AC 32 realizes that the patient has the DME and needs it, so the AC 32 continues to bill the payer in the hope of receiving the correct documentation from the provider before an audit from a certified audit entity or auditors 38, which can include a recovery audit contractor (RAC), occurs.
- payers 28 regularly audit ACs 32 through the use of auditors 38 that cost both the payer 28 and AC 32 time and fines. Medicare reports that auditors 38 succeeded in correcting more than $992,700,000 in Medicare® overpayments between March 2005 and March 2008, which is not limited to DME devices and does not include improper payments to private insurers.
- It has been estimated that about 30% of the 30 billion dollar DME industry represents fraudulent payments.

As is also shown in FIG. 2, there is a potential for a large number of unused devices to be delivered 44 from the AC 32 to the patient 36, and manual inspections of the DME are regularly performed 46 by the AC 32. As indicated above, documentation from the physician 30 to the AC 32 is often untimely and inaccurate 48. Also the auditors 38 often finds positive fraud audits 52 regarding the physician 32, and uncovers fraud in approximately 30% of AC 32 audits 50.

Figure 3:
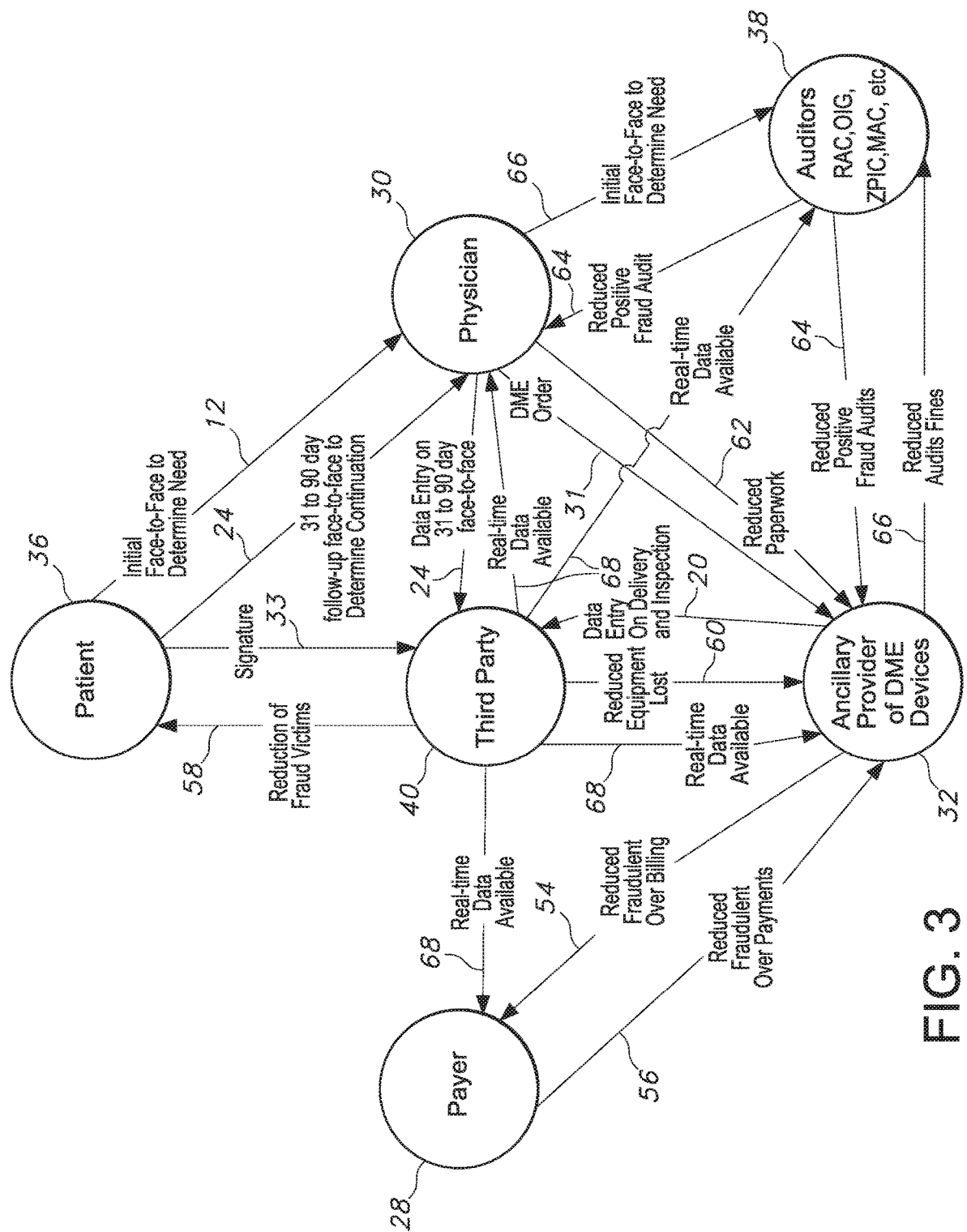
FIG. 3 is a relational diagram showing a patient validation process workflow in accordance with one or more embodiments disclosed herein.

The workflow 42 of the physician 30, patient 36, and AC 32 encounter will now be described using an embodiment of the method disclosed herein to prevent fraud associated with reimbursement concerning the provision and maintenance of DME, as shown in FIG. 3.

The patient 36 visits the physician 30 for an initial face-to-face meeting, which may or may not determine a need for a DME. If the physician 30 determines that there is a need for a DME to improve the patient's health the process continues through issuance of a DME prescription or order 31, and if the physician 30 determines that there is no need for a DME to improve the patient's health, the process ends.

If the physician 30 determines that there is a need for the DME to improve the patient's health, the AC 32 receives a prescription for the DME and supplies from the physician. The AC 32 affixes or tags the DME with a uniquely defined code. This code is a 256-bit advanced encryption system (AES) encrypted string, which includes the name of the AC 32, coordinated universal time code (UTC) date and time to the millisecond, which are encrypted using an additional secret key as a salt. A quick response (QR) or DataMatrix code image is then created using the secret key. The QR or DataMatrix code image is then encrypted so that only an application in accordance with one or more embodiments disclosed herein, which are referred to herein as a third-party application, can read the code. Any other QR or DataMatrix code reader, such as an i-Nigma code reader, will not be able to recognize the resulting code nor will it be possible to hack the encrypted code image. Even if the code is hacked, an encrypted value would be the result which is extremely difficult, if not impossible, to hack.

The AC technician then scans the QR or DataMatrix code that is affixed to the DME using the third-party application. The third-party application displays a form, questionnaire, and/or template that enables the AC technician to enter information associated with the DME that includes, but is not limited to, the following:
- manufacturer, make, model, serial number and/or lot number of the DME;
- latitude and longitude of the DME, as automatically captured by the third-party application using the GPS features associated with a mobile device on which the third-party application is executing;
- user identification, which represents an identity of the AC technician who performed the scan of the DME, is automatically captured;
- date and time of the scan of the DME is automatically captured;
- hours-of-operation are entered by the AC technician after reading the hours-of-operation from the DME; and
- picture image or video of hours-of-operation meter on the DME, as captured by the AC technician using a camera function of the mobile device on which the third-party application is executing, which is used as an audit mitigation measure.

The AC technician delivers the DME to the patient's location, such as the patient's home or office. The AC technician then scans the encrypted QR or DataMatrix code using the third-party application. The third-party application displays a form, questionnaire, or template that enables the AC technician to enter information concerning the patient 36 that includes, but is not limited to, the following:
- patient identifier, such as, but not limited to medical record number, Medicare® health insurance claim (HIC) number, and the like, which is used by the physician 30, payer 28, and AC 32 to properly correlate the patient journey;
- latitude and longitude of the patient, which is automatically captured by the third-party application using the GPS function of the mobile device on which the on which the third-party application is executing;
- user identification, which represents the identity of the person performing the scan of the DME and which is automatically captured;
- date and time of the scan, which is automatically captured;
- hours-of-operation as entered by the AC technician after reading the hours-of-operation from the DME hours-of-operation meter;
- picture image or video of hours-of-operation meter on the DME, which is captured by the AC technician using a camera function of the mobile device on which the third-party application is executing, which is also used as an audit mitigation measure; and
- in-home diagnostic testing and result gathering to capture additional functionality that may be requested by the physician, such as, but not limited to blood gasses, international normalized ratio (INR) Coumadin® testing, ventilators, spirometry, pulse oximetry, and the like.

The DME can automatically transmit data statistics concerning DME state and usage when the DME is coupled to a networked device. Not all DME can or will have network-enabled sensors. Network-enabled sensors include, but are not limited to, wireless phone networks, wireless home Internet networks, and the like. Built-in phone network sensor devices can enable the AC 32 to know where the DME is located when the DME is removed from the location to which the DME was delivered. Battery backup also allows the network-enabled sensor device to continue working as a location-monitoring device during loss of power or low power conditions. Information that the network-enabled sensor can automatically submit to a centralized data server includes, but is not limited to, the following:
- hours-of-operation as this value changes at any configurable interval;
- date and time or timestamp of a receipt of an on command associated with the DME;
- date and time or timestamp of an off command associated with the DME;
- airflow into the DME, which is updated at predetermined time periods, such as every second;
- airflow out of the DME, which is updated at predetermined time periods, such as every second;
- electrical current ratings, such as load and conditions associated with the DME, which are updated at predetermined time periods, such as every second; and
- latitude and longitude of the DME.

In one or more embodiments, non-limiting examples of which will be described in further detail below in conjunction with FIGS. 4 and 5, the DME is configured for two-way transmission of data and control signals over a communications network when coupled to a networked device for remotely controlling an operation of the DME, if such networked functionality is not already embedded into the DME itself. The network over which data and control signals are conveyed may comprise a wired communications network, including, but not limited to, Ethernet, fiber optic and other optical networks, cable, telephone, copper, etc., or the network may comprise a wireless communications network, including, but not limited to, a cellular network (e.g., 4G or 5G), satellite, radio frequency (RF), wireless local area network (WLAN), Bluetooth® (developed and managed by Bluetooth Special Interest Group, Inc.), terrestrial microwave, wireless ad hoc network (WANET), Wi-Fi (e.g., IEEE 802.11 Std.), WiMAX (e.g., IEEE 802.16 Std.), spread spectrum, free-space optical (FSO) communication, infrared, etc.

Embodiments disclosed herein enable real-time monitoring of information, which can be obtained automatically by network-enabled sensors or manually entered by using the third-party application including information regarding the delivery of the DME by the AC technician, physician 30, payer 28, auditors 38, and AC 32. The payer 28 can correlate the initial billing by the AC 32 against information made available by the embodiments disclosed herein. The physician 30 can subscribe to DME delivery information in order to integrate this information into the physician's electronic medical record (EMR) system.

Between 31 and 90 days following delivery of the DME, the patient 36 is required to have a face-to-face visit with the physician 30. The physician 30 scans the encrypted QR or DataMatrix code of the patient's DME using the third-party application. The third-party application then automatically shows the physician 30 a form, questionnaire, or template of fields requesting information required by the payer 28 to comply with patient outcomes, which includes, but is not limited to, the following:

- daily hours prescribed, which must be entered by the physician 30, and represents how many hours (1-24) that the patient must use the DME;
- physician comments, which are entered by the physician 30 concerning the face-to-face visit with the patient;
- whether the patient 36 is present for a 90-day visit, to which the physician 30 is to answer "yes" or "no";
- whether the compliance download has been read by the physician 30, to which the physician 30 is to answer "yes" or "no";
- daily hour usage, which can be calculated automatically, and represents how many hours a day the patient has used the DME;
- days of usage, which can be automatically calculated, and represents how many days the patient has used the DME;
- whether the patient 36 is benefiting from use of the DME, to which the physician 30 is to answer "yes" or "no";
- whether the patient 36 needs to continue use of the DME;
- whether the patient 36 is non-compliant with the prescribed usage of the DME, yet has been re-instructed to use it correctly, to which the physician 30 is to answer "yes" or "no";
- patient's signature, in response to which the patient 36 is to sign 33 a signature screen signifying the patient's agreement with data entered by the physician 30;
- hours-of-operation, to which the physician 30 enters the number of hours-of-operation from the meter on the DME, which is used to calculate average daily hours-of-operation to determine whether the patient 36 is compliant with the daily hours of use prescribed by the physician 30;
- hours-of-operation picture image or video, to which the physician 30 responds by using a camera function of the mobile device on which the third-party application is executing to capture an image or video of the hours-of-operation meter on the DME, which is used as an audit mitigation measure;
- latitude and longitude, which is automatically captured by the third-party application using a GPS function of the mobile device on which the third-party application is executing;
- user identification of the person performing the scan, which is automatically captured;
- date and time of the scan, which is automatically captured;
- patient verification, which is performed by the physician 30 by verifying the patient identifier; and DME device verification, which is verified by the physician 30 by verifying the DME information that includes, but is not limited to, manufacturer, make, model, serial number and/or lot number associated with the DME.

The DME can automatically transmit data statistics concerning DME state and usage when coupled to a networked device. Not all DMEs can or will have network-enabled sensors. Network-enabled sensors may be, but are not limited to, wireless phone networks, wireless home Internet networks, and the like. Built-in phone network sensor devices can enable the AC to know where the device is located when removed from the location at which the DME was delivered. Battery backup also allows the network-enabled sensor device to continue working as a location device in the absence of power or during low power conditions. Information to be automatically submitted to a centralized data server may include, but is not limited to, the following:

- hours-of-operation as this value changes at any configurable interval;
- date and time or timestamp of a receipt of an on command associated with the DME;
- date and time or timestamp of an off command associated with the DME;
- airflow into the DME, which is updated at predetermined time periods, such as every second;
- airflow out of the DME, which is updated at predetermined time periods, such as every second;
- electrical current ratings; such as load and conditions associated with the DME, which are updated at predetermined time periods, such as every second; and
- latitude and longitude of the DME.

Information is automatically made available to the physician 30, payer 28, auditors 38, and AC 32 in real-time by network-enabled sensors or manual entry through the use of the third-party application. As a result, the AC 32 can bill immediately without the delay of waiting for documents from the physician 30. The payer can correlate bills from the AC 32 with data available from a third-party resource, such as a server. The auditors 32 can analyze the data available from the third-party resource for pattern recognition of fraudulent activities. This can include predictive analytics as well as regional trend correlations. The payer can wait for positive notification from the auditors 38 before payment is issued to the AC 32 and/or physician 30.

The AC technician visits the patient in accordance with a regular schedule to check if the DME is still working and to perform any regular maintenance. At this time, the AC technician scans the DME device encrypted QR or DataMatrix code using the third-party application. The application then displays a form, questionnaire, or template with fields that are to be completed by the AC Technician, which include, but are not limited to, the following:

- hours-of-operation, for which the physician enters the number of hours-of-operation from the meter on the DME, which is used to calculate average daily hours-of-operation to determine whether the patient 36 is compliant with the prescribed daily hours of use by the physician 30;
- hours-of-operation picture image or video, which is captured by the physician 30 using the camera function of the mobile device on which the third-party application is executing, to take a picture of the hours-of-operation meter on the DME, which is also used as an audit mitigation measure;
- latitude and longitude, which is automatically captured by the third-party application using the GPS function of the mobile device on which the third-party application is executing; user identification of the person performing the scan, which is automatically captured;
- date and time of the scan, which is automatically captured;
- patient verification, which is performed by the AC technician who verifies the patient identifier; and DME verification, which is performed by the AC technician who verifies the DME information, and includes, but is not limited to, the manufacturer, make, model, serial number, and/or lot number associated with the DME; and in-home diagnostic testing and result gathering to capture additional functionality that may be requested by the physician, such as, but not limited to blood gasses, international normalized ratio (INR) coumadin testing, ventilators, spirometry, pulse oximetry, and the like.

The DME can automatically transmit data statistics concerning the DME state and usage when coupled with a network-enabled device. Not all DME can or will have network-enabled sensors. Network-enabled sensors may include, but are not limited to, wireless phone networks, wireless home Internet networks, and the like. Built-in phone network sensor devices can enable the AC 36 to know where the DME is located when removed from the location to which the DME was delivered. Battery backup also allows the network-enabled sensor to continue working as a location device without power or during low power conditions.

Information that can automatically be submitted to a centralized data server may include, but is not limited to, the following:

hours-of-operation as this value changes at any configurable interval;

date and time or timestamp of a receipt of an on command associated with the DME;

date and time or timestamp of an off command associated with the DME; airflow into the DME, which is updated at predetermined time periods, such as every second;

airflow out of the DME, which is updated at predetermined time periods, such as every second;

electrical current ratings, such as load and condition associated with the DME, which are updated at predetermined time periods, such as every second; and latitude and longitude of the DME.

The third-party makes information, as verified using, for example, the patient's signature 22 and/or GPS coordinates, available automatically by network-enabled sensors or manual entry through the use of the third-party application including patient usage patterns and/or DME performance to the physician 30, payer 28, auditors 36, and AC 32. If the physician 30 determines that the patient 36 is not benefiting or does not need to continue use of the DME, the AC technician visits the patient 36 to acquire the DME, where it is located, or the patient may deliver the DME to the AC office. The AC technician scans the encrypted QR or DataMatrix code on the DME to verify DME device information, verify the patient information, and change the value of the decommission form field from "no" to "yes". The AC technician returns the DME to the ACs office or warehouse and creates a new encrypted QR or DataMatrix code for the returned DME, which enables the process to begin again with respect to a particular DME. The same encrypted QR or DataMatrix code is not to be reused once it has been decommissioned from a patient and DME, which avoids the potential for confusion between the encrypted QR or DataMatrix codes.

In addition to the features discussed above, embodiments of the invention incorporate and can be used in conjunction with any or all of the following while remaining within the intended scope:

wired and wireless networks;

software, firmware, assembly code, and machine code, wherein software is used herein to refer to any or all of the aforementioned instruction formats;

any and all network protocols;

any network device or resource including, but not limited to, network switches, routers, gateways, and storage switches; and steps of the embodiments are capable of being performed in any order.

As shown in FIG. 3, the embodiments disclosed herein enable a substantial reduction or elimination of errors concerning the misdirection and/or non-delivery of treatment using DME, as well as fraudulent overbilling 54 and overpayment 56, which are currently prevalent. These embodiments also result in significant reductions in victims 58, lost equipment 60, documentation and paperwork 62, positive audits 64, and audit fines 66. In addition, these embodiments provide for real-time data availability 68 to the payer 28, physician 30, AC 32, and auditors 38.

Fraudulent activity associated with durable medical equipment is widespread. For example, in August 2011, a jury in Los Angeles convicted three defendants, a durable medical equipment (DME) owner, his wife, and an employee, for their roles in billing Medicare $14.2 million in fraudulent DME claims after a two-week trial. According to trial evidence, the owner and his wife were pastors of a Los Angeles area church where they also operated a DME supply company. The defendants purchased fraudulent prescriptions and documents, including Medicare numbers and identities of beneficiaries, including dead beneficiaries, from illicit sources to bill Medicare for expensive, high-end power wheelchairs and orthotics that were medically unnecessary or never provided. When it appeared that the owner would have to close the DME company due to an audit by Medicare, the owner persuaded his sister and a member of the church to allow him to use their names and identities to open two new fraudulent DME companies. After closing the first DME company, the defendants and their co-conspirators continued to operate the fraud scheme from the two new fraudulent DME companies. Two co-defendants pleaded guilty previously and three defendants were convicted at trial in August 2011.

In July 2011, a jury in Los Angeles convicted the co-owner of a DME company and a purported home health agency for his role in causing approximately $11.9 million in fraudulent DME billings and $8 million in fraudulent home health billings to Medicare. The DME co-owner and a second co-owner conspired with others to defraud Medicare by paying marketers for access to Medicare beneficiary information and fraudulent documents in order to submit and cause the submission of false claims to Medicare for DME and home health services that were not medically necessary, and that often were not provided at all. The second co-owner pleaded guilty prior to the trial to multiple health care fraud charges in connection with his participation in the scheme.

In May 2011, the U.S. District Court in Houston sentenced the owner of a Houston-area DME company to 84 months in connection with a $2 million Medicare fraud scheme. A DME company co-conspirator was sentenced to 70 months in prison. The DME owner admitted that she paid kickbacks, sometimes $1,000 per patient, to recruiters who brought patients to her DME company. The owner then billed Medicare for medical equipment that the patients either did not need or never received, including power wheelchairs and orthotic devices. A physician co-conspirator was sentenced to 41 months in prison. Two patient recruiters were sentenced to 46 months in prison.

In February 2011, the court sentenced a DME owner/manager to 57 months in prison in connection with a $2.8 million conspiracy to commit health care fraud. The defendant billed Medicare for arthritis kits for more than 683 beneficiaries, some of whom were deceased. None of the beneficiaries interviewed knew of the defendant, the co-defendant, or the DME provider. A physician co-conspirator signed purported prescriptions ordering DME that served as the basis for the owner's fraudulent claims to Medicare. A third co-conspirator who was charged in a separate case pleaded guilty.

In November 2010, a court sentenced a manager of a Houston-area DME company to 120 months in prison for his role in a $1.1 million Medicare fraud scheme. The defendant submitted false claims to Medicare for power wheelchairs and accessories as catastrophe related in connection with Hurricanes Katrina, Rita, Ike, and Gustav. Many of the Medicare beneficiaries, including some who testified at trial, had never owned a power wheelchair during these catastrophes or had owned one that was damaged during these catastrophes. According to trial evidence, the defendant was previously convicted of fraud, and he failed to admit that previous conviction on documents he submitted to Medicare. A co-defendant who was a DME delivery driver was sentenced to 41 months in prison for delivering medically unnecessary DME, including power wheelchairs, to Medicare beneficiaries whom he knew did not need, and in some cases did not even want the DME.

In January 2011, a physician and five other individuals in Texas were sentenced to 41 months, 21 months, 26 months, 46 months, 70 months, and 41 months of incarceration, respectively, for their roles in a multi-million dollar DME fraud scheme. Two others were sentenced to 10 months of community service and home confinement and 3 years of probation. respectively. Evidence presented at trial showed that from 2003 to 2009, these individuals billed Medicare for fraudulent DME, including power wheelchairs and orthotic devices. The physician ratified prescriptions for medically unnecessary DME, while others created fraudulent patient files, paid kickbacks to recruiters, and delivered DME, such as power wheelchairs and orthotics, to beneficiaries who had no medical need for the equipment. The owner of the DME and the other remaining defendants have pleaded guilty for their participation in various parts of the fraud scheme.

In August 2011, following a two-week trial, a jury in Baton Rouge found guilty all four defendants in a $4.7 million Medicare fraud. Trial evidence established that between 2003 and 2009, the owner/operator of a Baton Rouge area DME company paid two patient recruiters to locate and solicit Medicare beneficiaries to attend health fairs hosted at churches and other locations. At the health fairs, doctors prescribed the beneficiaries power wheelchairs that were medically unnecessary. The DME owner then used the prescriptions to submit false and fraudulent claims to Medicare. The patient recruiters paid the doctors illegal kickbacks based on the number of power wheelchair prescriptions generated at the health fairs. The DME owner also paid kickbacks to the recruiters on a per prescription basis when beneficiaries received prescriptions for medically unnecessary power wheelchairs for which the owner's company fraudulently billed Medicare.

In June 2011, the District Court in Baton Rouge sentenced an owner of a Baton Rouge DME company to 60 months in prison for his role in a $5.4 million health care fraud scheme.

The DME owner and three co-conspirators admitted to their roles in a multi-year scheme to defraud Medicare by routinely submitting claims to Medicare seeking reimbursement for a set of expensive braces (including a back brace, knee braces, and other items) when they knew that the braces were not medically necessary and had not been prescribed for the beneficiaries by their physicians. The court sentenced one coconspirator to 48 months in prison, a second to 30 months in prison, and another to 24 months probation.

In January 2011, a court sentenced a DME owner/operator to serve 48 months in prison for his role in a $775,000 DME fraud scheme. The court sentenced the co-defendant, a physician, to 30 months in prison. The physician wrote prescriptions for medically unnecessary DME, such as power wheelchairs, wheelchair accessories, and feeding nutrients. The majority of the DME company's fraudulent claims were based on prescriptions for medically unnecessary DME that were written and provided by the physician.

In May 2011, the United States District Court for the Middle District of Tennessee entered a judgment of $82.6 million in favor of the United States in a FCA case alleging that Renal Care Group (RCG), Renal Care Group Supply Company (RCGSC) and Fresenius Medical Care Holdings, Inc. violated the FCA when they submitted claims from 1999 through 2005 to the Medicare program for home dialysis supplies provided to patients with end stage renal disease (ESRD) for reimbursement of the supplies and equipment.

All of these claims, as well as related claims for support services rendered by RCG dialysis clinics were false because the defendants were prohibited from and not qualified to bill Medicare for these home dialysis patients. Under Federal law, the Medicare program pays companies that provide dialysis supplies to patients only if the companies that provide the supplies are truly independent from dialysis facilities and the ESRD patient chooses to receive supplies from the independent supply company. The government alleged that the defendants set up a sham billing company, RCGSC, which was not independent from RCG. Further, RCG interfered with ESRD patients' choice of supply options, requiring patients to move to RCGSC. Even after RCG employees raised concerns and industry competitors closed their supply companies, RCG kept RCGSC open because of the illicit revenue it created.

In September 2011, Hill-Rom Company, Inc (Hill-Rom), a national DME supplier, paid the United States $41.8 million to resolve allegations that Hill-Rom submitted false Medicare claims for bed support surfaces for patients who no longer needed or were no longer using this DME. Bed support surfaces are generally used to relieve pressure on bed-bound patients suffering wounds or other sores.

In May 2011, the owner and operator of a Florida pharmacy was sentenced to 52 months incarceration for health care fraud. Between August 2006 and April 2007, the individual used his pharmacy to submit false claims to Medicare, including claims for deceased beneficiaries. These claims sought reimbursement for the cost of DME prescription medications, and other items and services for Medicare beneficiaries in Florida that were not prescribed by doctors or provided as claimed.

In May 2011, a Florida man was sentenced to 55 months incarceration for defrauding the Medicare program. Between July 2006 and January 2007, the individual, the owner of a DME supply company, caused the company to submit false and fraudulent Medicare claims for DME items such as pressure support ventilators, therapy pumps, and other DME that were not prescribed by physicians nor received by Medicare beneficiaries.

In October 2010, a consent judgment was entered against a defendant for $657,708 for causing the submission of false claims by the defendant's former company, Orthoscript. Inc., to Medicare, TRICARE, and FEHBP from 1999 through 2004. Orthoscript improperly billed the programs under the wrong, higher paying codes for certain DME. The defendant was earlier tried and convicted for fraud in connection with the scheme.

As previously stated, in one or more embodiments, the DME is configured to provide two-way communications over a communication network to remotely access information and/or control an operation of the DME. By way of illustration only and without limitation, FIG. 4 is a block diagram conceptually depicting at least a portion of an exemplary DME apparatus 70 configured for two-way communications, according to one or more embodiments of the invention. In this illustrative embodiment, the DME apparatus 70 is a continuous positive airway pressure (CPAP) device which may be prescribed to treat sleep apnea in a patient. With reference to FIG. 4, the DME apparatus 70 includes a face mask 71 adapted to be secured over the patient's nose. The face mask 71 is coupled to a blower 72 via a flexible airway (e.g., tubing) 73. The blower 72 is adapted to produce a controllable high-speed airflow, through the airway 73, into the upper respiratory tract of the patient to form a positive air pressure. The blower 72 is connected to a motor driver circuit 74 which generates an output voltage for controlling a speed of the blower as a function of a control signal supplied by a microcontroller 75 operatively coupled to the motor driver circuit.

The DME apparatus 70 preferably includes one or more sensors 76, including pressure and temperature sensors that monitor the pressure and temperature, respectively, of the airflow generated by the blower 72 and delivered to the patient through the face mask 71. In one or more embodiments, the sensors 76 include a blood oxygen sensor (e.g., pulse oximeter) for monitoring the oxygen saturation level in the blood of the patient. The oxygen sensor in the sensors 76 may be used to generate an apnea hypoxia index (AHI) associated with the patient. The AHI is a standard index used to indicate the severity of sleep apnea; the AHI is represented by the number of apnea and hypopnea events per hour of sleep. An attending physician or other healthcare provider may remotely access the DME apparatus 70 to obtain the AHI of the patient, either in real-time or historical AHI data, or other patient physiological information, which may be stored in the DME.

This temperature, pressure and/or oxygen saturation information generated by the sensors 76 is provided to the microcontroller 75 through a first interface module 77. The first interface module 77 may comprise signal conditioning and/or translation circuitry, such as, for example, an amplifier, filter, analog-to-digital converter (ADC), voltage translator/level shifter, etc., for generating a signal or signals indicative of the temperature and pressure of the airflow and/or patient blood oxygen saturation level in a form compatible with the microcontroller 75. In some cases, the microcontroller 75 will include signal conditioning circuitry embedded therein, thus eliminating the need for the first interface module 77.

The microcontroller 75 utilizes the sensor information obtained from the sensors 76 as part of an active feedback loop, for example, to control a speed or other parameter of the blower, and thereby increase or decrease the volume of airflow generated by the DME apparatus 70 as appropriately prescribed for treating the patient. This closed-loop feedback mechanism will cause the blower 72 to continuously vary the air pressure delivered by the blower in order to maintain a prescribed constant pressure at the face mask 71.

The DME apparatus 70 optionally comprises an air conditioning module 78, which in this embodiment includes a heater and/or humidifier, operatively connected in the airway 73. The air conditioning module 78 is controlled by the microcontroller 75 through a second interface module 79. The second interface module 79 may comprise signal conditioning and translation circuitry, such as, for example, a digital-to-analog converter (DAC), voltage translator/level shifter, etc., for generating a control signal or signals in a form compatible with the air conditioning module 78 for controlling the temperature and/or humidity of the air supplied to the patient. In this embodiment, the sensors 76 preferably also includes a humidity sensor which monitors the humidity levels of the air supplied to the patient. The microcontroller 75 uses this air humidity information, along with air temperature information provided by the temperature sensor, as part of an active feedback loop including the second interface module 79 and air conditioning module 78 to achieve a comfortable temperature and humidity of the air supplied to the patient.

An input/output (I/O) interface 80 is preferably connected with the microcontroller 75. The I/O interface 80 functions as a mechanism for supplying input data to the microcontroller 75 by a user for locally controlling an operation of the DME apparatus 70 and for locally outputting data generated by the microcontroller for presentation to the user. The I/O interface 80 may include, for example, one or more input devices, such as, but not limited to, a keyboard or keypad, mouse, etc., and one or more output devices, such as, but not limited to, a display (e.g., monitor), audio presentation device (e.g., speaker), etc. In one or more embodiments, the I/O interface 80 comprises a liquid crystal display (LCD) panel attached to the DME apparatus 70 for displaying the operational status and other information associated with the DME.

In order to provide two-way communications functionality with a remote user, the DME apparatus 70 preferably includes a communications module 81 (e.g., a network server) connected to the microcontroller 75 and to a communication network 82; the communications module 81 provides an interface between the microcontroller 75 and the communication network 82. As previously stated, the network 82 over which data and control signals are conveyed may comprise a wired or wireless communications network employing a standard or proprietary communications protocol, including, but not limited to, Ethernet, fiber optic and other optical networks, cable, telephone, copper, a cellular network (e.g., 4G or 5G), satellite or RF transmission, wireless local area network (WLAN), Bluetooth®, terrestrial microwave link, wireless ad hoc network (WANET), Wi-Fi (e.g., IEEE 802.11 Std.), WiMAX (e.g., IEEE 802.16 Std.), spread spectrum, free-space optical (FSO) communication, infrared, etc.

In one or more embodiments, the communications module 81 includes a transmitter for sending data generated by the microcontroller 75 and/or stored in a memory of the DME that is indicative of an operation and/or status of the DME apparatus 70 over the communication network 82; such information may be real-time or stored historical data. The communications module 81 also comprises a receiver for receiving data supplied to the DME apparatus 70, either for requesting the DME apparatus to send information regarding the status and/or operation of the DME, or for controlling an operation and/or parameter of the DME by the remote user. In some embodiments, the communications module 81 comprises a transceiver that integrates the functions of both the transmitter and the receiver.

Data generated by the microcontroller 75 may be automatically sent to a remote user over the network 82; that is, without any action required on the part of the remote user. Alternatively, the microcontroller 75 may be configured to receive, via the communications module 81, a request for data sent by the remote user over the network 82. For example, in one or more embodiments, the microcontroller 75 may be configured to automatically transmit DME and/or patient status information (e.g., airflow pressure, air temperature, AHI, DME diagnostics, etc.) over the network 82 at prescribed intervals (e.g., every four hours). In one or more other embodiments, the microcontroller 75 may be configured to transmit status information over the network 82 in response to a request signal sent by the remote user to the DME apparatus 70.

In some instances, such as, for example, telehealth applications, it may be beneficial for an attending healthcare provider to make certain modifications to a DME prescription without the need to have the patient schedule an in-person office visit. By way of example only, based on patient usage and/or status information obtained remotely from the DME apparatus 70 by the patient's attending physician over the network 82, the physician may desire to change the airflow pressure generated by the DME. For instance, if the DME usage information indicates that the patient is still showing signs of sleep apnea or hypoxia, the airflow pressure to the patient may need to be increased by a prescribed amount. To accomplish this, the physician may transmit a control signal over the network 82 which is received by the communications module 81 of the DME apparatus 70 coupled to the network. This control signal received by the DME apparatus 70 from the remote attending physician is then supplied to the microcontroller 75. In response, the microcontroller 75 sends a signal to the motor driver circuit 74 for controlling the blower 72 as a function of the control signal received remotely from the physician. In this manner, the airflow pressure supplied to the patient by the DME apparatus 70 can be beneficially adjusted remotely by the attending physician in real-time. The physician can confirm whether or not the prescribed change has improved the patient's condition by monitoring the patient DME usage status and physiological condition (e.g., AHI) and make modifications to the DME apparatus in real-time, all performed remotely.

Figure 5:
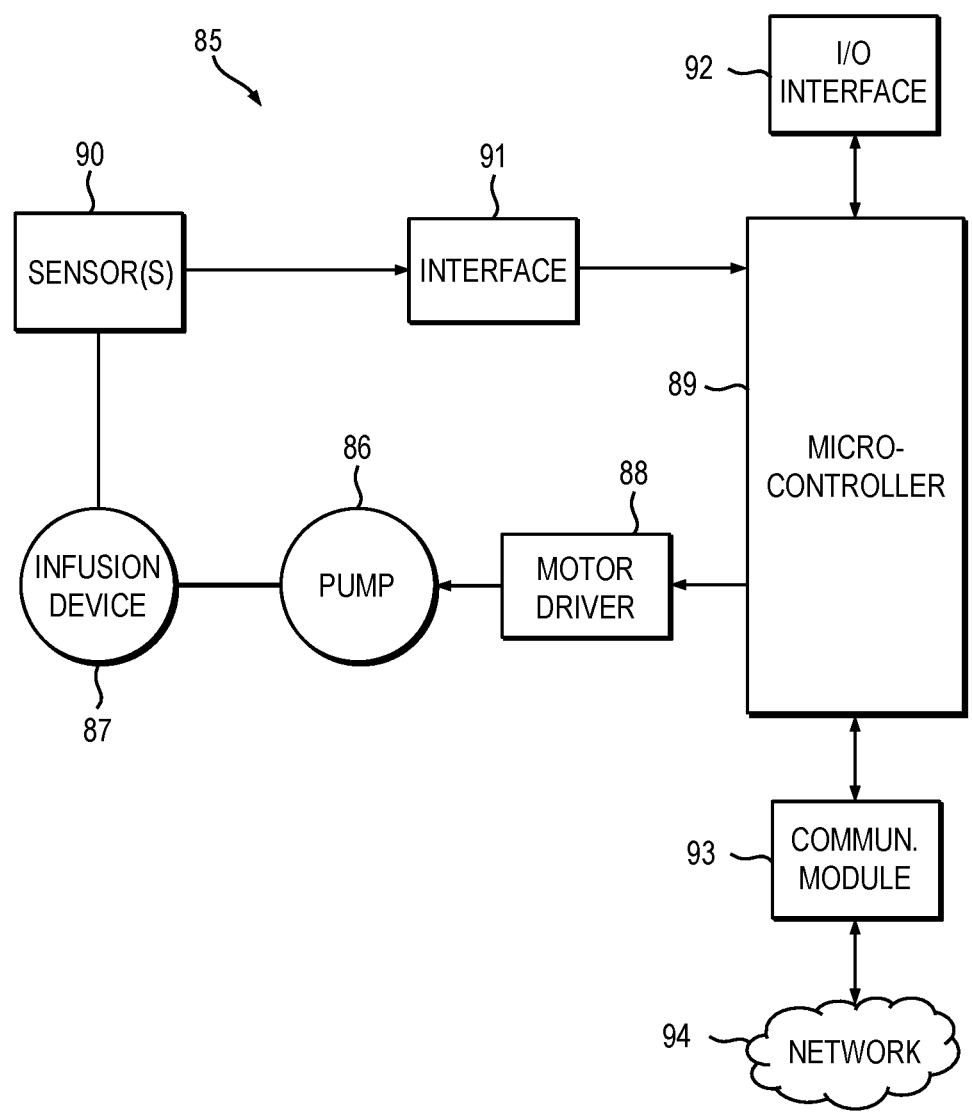
FIG. 5 is a block diagram depicting at least a portion of an exemplary DME apparatus configured for two-way communications, in accordance with an alternative embodiment of the invention.

FIG. 5 is a block diagram conceptually depicting at least a portion of an exemplary DME device 85 configured to provide two-way communications with a remote user, according to another embodiment of the invention. In this embodiment, the DME device 85 is an insulin pump which may be used to treat diabetes or otherwise manage blood sugar levels in a patient. As shown in FIG. 5, the DME device 85 comprises a pump 86 adapted to deliver insulin (or another prescribed drug) into the bloodstream of the patient through an infusion device 87 in contact with the patient. The pump 86 is controlled by a motor driver circuit 88 as a function of a signal generated by a microcontroller 89 which is connected with the motor driver circuit.

The DME device 85 includes at least one sensor 90, which in this embodiment comprises one or more blood sensors, adapted to monitor at least one parameter of the patient's blood, such as, for example, blood sugar level. The blood sensors 90 will generate a signal or signals indicative of the monitored blood parameter(s) (e.g., blood sugar level) and supply this information to the microcontroller 89 through an interface module 91. The interface module 91 may comprise signal conditioning and/or translation circuitry, such as, for example, an amplifier, filter, analog-to-digital converter (ADC), voltage translator/level shifter, etc., for generating a signal or signals indicative of the monitored blood parameter(s) in a form compatible with the microcontroller 89. The microcontroller 89 utilizes this blood parameter information as part of an active feedback loop, for example, to control a volume and/or frequency of the drug delivered by the pump 86, as appropriately prescribed for the patient. This closed-loop feedback mechanism will cause the pump 86 to maintain the monitored blood parameter(s) at a prescribed level.

Figure 4:
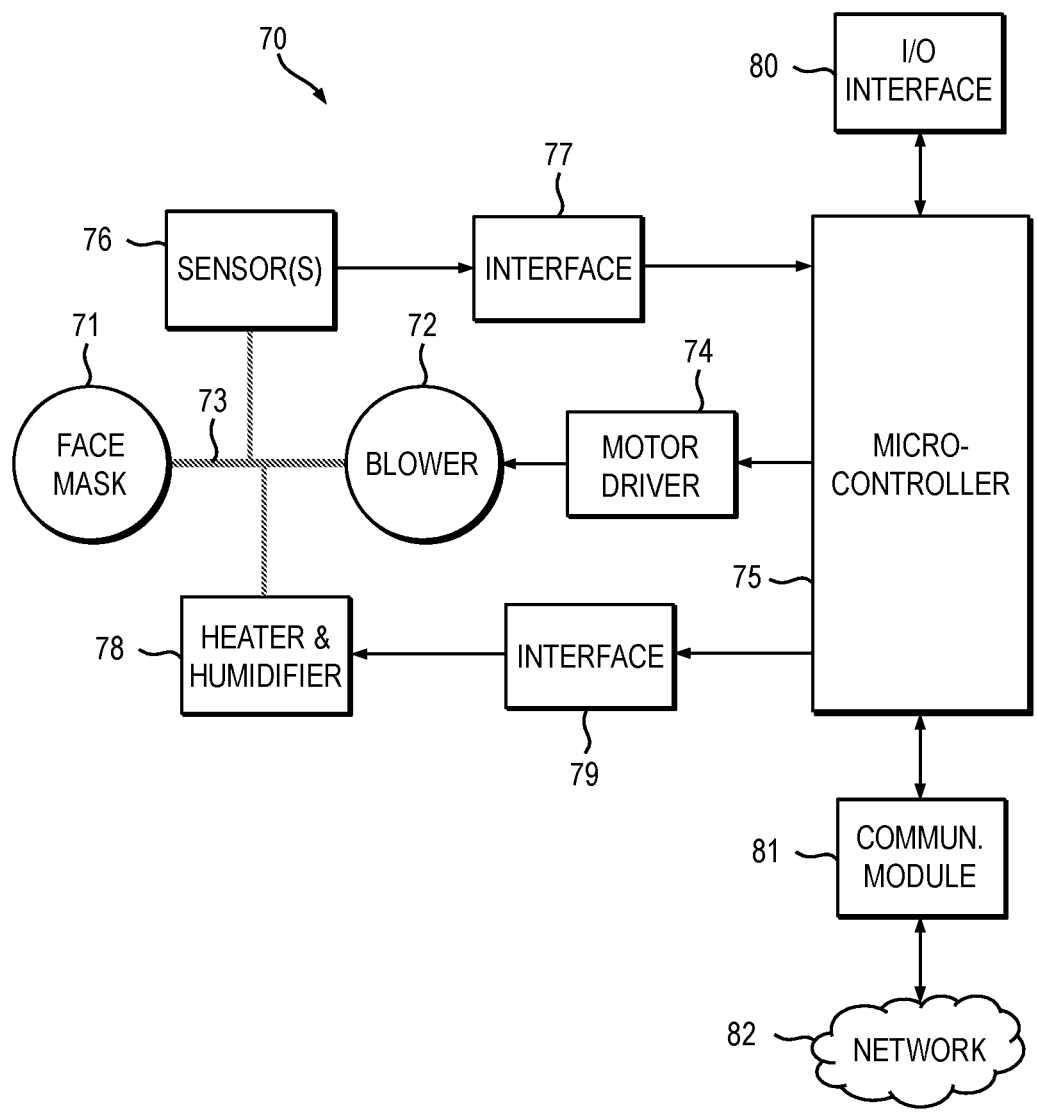
FIG. 4 is a block diagram depicting at least a portion of an exemplary DME apparatus configured for two-way communications, in accordance with one or more embodiments of the invention.

Like the illustrative DME apparatus 70 shown in FIG. 4, the DME device 85 preferably includes an I/O interface 92 connected to the microcontroller 89. The I/O interface 92 is configured to supply input data to the microcontroller 89 by a user for controlling an operation of the DME device 85 and/or for outputting data generated by the microcontroller for presentation to the user. The I/O interface 92 may include, for example, one or more input devices (e.g., keyboard or keypad, mouse, etc.) and/or one or more output devices (e.g., display/monitor, speaker, etc.).

The DME device 85 further includes a communications module 93 (e.g., network server) connected to the microcontroller 89 and to a communication network 94 for providing two-way communications functionality with a remote user, as described in conjunction with the exemplary DME apparatus 70 shown in FIG. 4. As previously stated, the network 94 over which data and/or control signals are conveyed between the DME device 85 and a remote user may comprise a wired and/or wireless communications network, including, but not limited to, Ethernet, fiber optic and other optical networks, cable, telephone, copper, a cellular network (e.g., 4G or 5G), satellite or RF transmission, wireless local area network (WLAN), Bluetooth®, terrestrial microwave link, wireless ad hoc network, Wi-Fi (e.g., IEEE 802.11 Std.), WiMAX (e.g., IEEE 802.16 Std.), spread spectrum, free-space optical (FSO) communication, infrared, etc.

In one or more embodiments, the communications module 93 includes a transmitter for sending data generated by the microcontroller 89 that is indicative of an operation and/or status of the DME apparatus 85 over the communication network 94. The communications module 93 also includes a receiver for receiving data supplied to the DME device 85, either for requesting the DME device to send information regarding the status and/or operation of the DME, or for controlling an operation and/or parameter of the DME by the remote user. In some embodiments, the communications module 93 includes a transceiver configured to implement the functions of both the transmitter and receiver.

Data generated by the microcontroller 89 may be automatically sent to a remote user over the network 94; that is, without any action required on the part of the remote user. Alternatively, the microcontroller 89 may be configured to receive, via the receiver in the communications module 93, a request for data sent by the remote user over the network 94. For example, in one or more embodiments, the microcontroller 89 may be configured to automatically transmit status information (e.g., blood sugar level, etc.) over the network 93 at prescribed intervals (e.g., every three hours). In one or more other embodiments, the microcontroller 89 may be configured to transmit DME status information, either real-time or stored historical data, over the network 94 in response to a status request signal sent by the remote user to the DME device 85.

By way of example only and without limitation, in a telehealth application it may be beneficial for an attending healthcare provider to make certain modifications to a DME prescription without the need to have the patient schedule an in-person office visit. For instance, based on patient blood sugar level information remotely obtained from the DME device 85 by the patient's attending physician over the network 94, the physician may desire to change the drug delivery frequency and/or delivered drug amount by the DME device 85. To accomplish this, the physician may transmit a control signal over the network 94 which is received by the communications module 93 of the DME device 85 coupled to the network. This control signal received by the DME device 85 from the remote attending physician is then supplied to the microcontroller 89. In response, the microcontroller 89 sends a signal to the motor driver circuit 88 for controlling the pump 86 as a function of the control signal received remotely from the physician. In this manner, the amount and/or delivery frequency of the prescribed drug supplied to the diabetic patient by the DME device 85 can be beneficially controlled remotely by the attending physician without having the patient come in for an in-person visit. The physician can confirm whether or not the prescribed change has improved the condition of the patient by monitoring the patient's blood sugar levels and making remote modifications to the DME device 85 in real-time.

Figure 6:
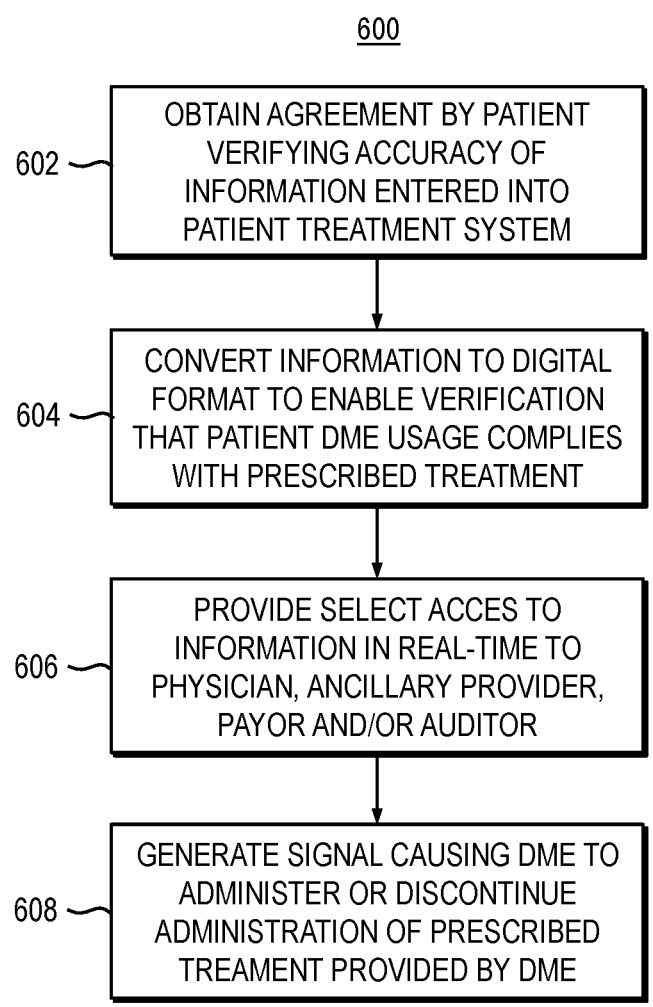
FIG. 6 is a flow diagram depicting at least a portion of an exemplary method for operating a patient treatment system incorporating a DME apparatus configured for two-way communications, in accordance with one or more embodiments of the invention.

With reference now to FIG. 6, a flow diagram depicts at least a portion of an exemplary method 600 for operating a patient treatment system incorporating a DME apparatus configured for two-way communications (e.g., consistent with the illustrative DME apparatus 70 and 85 shown in FIGS. 4 and 5, respectively), in accordance with one or more embodiments of the invention. In step 602, the patient treatment system obtains information that is input into a network server or other information repository and is associated with a patient, DME, a physician and/or an ancillary provider. In one or more embodiments, the information comprises an agreement by the patient verifying an accuracy of data entered into the patient treatment system by the physician, including at least one of (i) whether the patient is benefitting from use of the DME, (ii) whether continued use of the DME by the patient is required, (iii) the hours of operation of the DME, and (iv) a measure of the efficacy (at least in terms of quality and/or results) of the treatment (e.g., AHI, blood sugar levels, etc.).

In step 604, this information obtained in step 602 is converted into a digital format to enable verification that the information regarding patient DME usage, etc., complies with prescribed treatment associated with the DME. In step 606, selective access to the information obtained in step 602 is provided, in real-time, to the physician, ancillary provider, a payor and/or an auditor.

In step 608, the patient treatment system, through a remote person or entity having access to the DME over a communications network with which the DME an established connection, generates a control signal causing the DME to automatically administer or discontinue administration of a prescribed treatment using the DME. Such treatment may include, for example, providing airway pressure, air, oxygen, transcutaneous electrical nerve stimulation, continuous passive motion, mobility assistance, parenteral nutrition, enteral nutrition, dialysis, insulin, etc., to the patient. As a part of the administration of treatment in step 608, the remote person or entity may generate a signal, transmitted over the network to the DME, which causes the DME to automatically change certain parameters of its operation. For example, as described in conjunction with the illustrative CPAP device 70 shown in FIG. 4, the remote user (e.g., physician) may send a control signal to the DME, over a communications network, to cause the CPAP device to automatically change a pressure setting on the CPAP device to control the amount of airflow supplied to the patient. The physician/user can then remotely access the CPAP device, through the communications network, to obtain real-time AHI readings or other diagnostic information to confirm that the requested change has been implemented and has improved the patient's condition. In this manner, the healthcare provider can ensure a prescribed usage of the DME by the patient without having the patient physically come into the office.

Transmitting medical data within a home-care environment is significantly beneficial to advanced providers and other members of a patient's clinical team. Such information shows not only if the patient is compliant in using the DME as prescribed, but can also serve as an indicator of whether the patient is safely benefitting from their prescribed therapy. The following non-limiting examples are provided to show how aspects of the invention can be applied within the clinical application and ongoing assessment setting.

CPAP Therapy—collects an average and low AHI, which can directly note the clinical improvement by correlating the original AHI prior to and following the initiation of CPAP therapy; the AHI should be decreased following the initiation of CPAP therapy or following an increase in the patient's prescribed positive airway pressure (PAP) setting.

Automatic Positive Airway Pressure (APAP) Therapy—collects data similar to that seen in CPAP therapy, but adds additional clinical benefits to both assessment and management of the patient's response to the prescribed therapy settings. An APAP device fluctuates the PAP level continuously to meet the minimum pressures needed to prevent the airways from collapsing during exhalation. The data collected, which shows these pressure ranges, can be greatly beneficial both in showing a patient's positive response to the therapy and, more importantly, when the patient's response is poor. As the "mean PAP" continues to increase over time, this data can serve as an early indicator of a worsening of the patient's pulmonary status and/or need for additional support such as bi-level positive airway pressure (BiPAP) or non-invasive positive pressure ventilation.

Non-Invasive Ventilation (NIV)—often reserved for the most chronically ill of the respiratory home-care patient population. NIV is comprised of three to four pressures which are either fixed or fluctuating based off the patient's needs. The fluctuating pressures represent not only the PAP needed to keep the airways from collapsing during exhalation, but also the inspiratory pressure support needed to achieve a pre-set desired tidal volume (optimal volume in the lungs). The data transmitted is critical in helping to manage these often difficult patients by allowing the provider to identify early warning signs of an exacerbation. As the pressure needed to achieve the desired tidal volume increases, especially in cases where the pressures remain higher than minimum, the provider could use this information to consider increasing NIV support settings and even adding medications such as long-acting bronchodilators, corticosteroids and even diuretics to the patient's overall care plan.

Although illustrative embodiments of the invention have been described herein in the context of CPAP and insulin pump DME applications, it is to be understood that aspects according to embodiments of the invention can be easily modified for use with various other applications, as will become apparent to those skilled in the art given the teachings herein.

Figure 7:
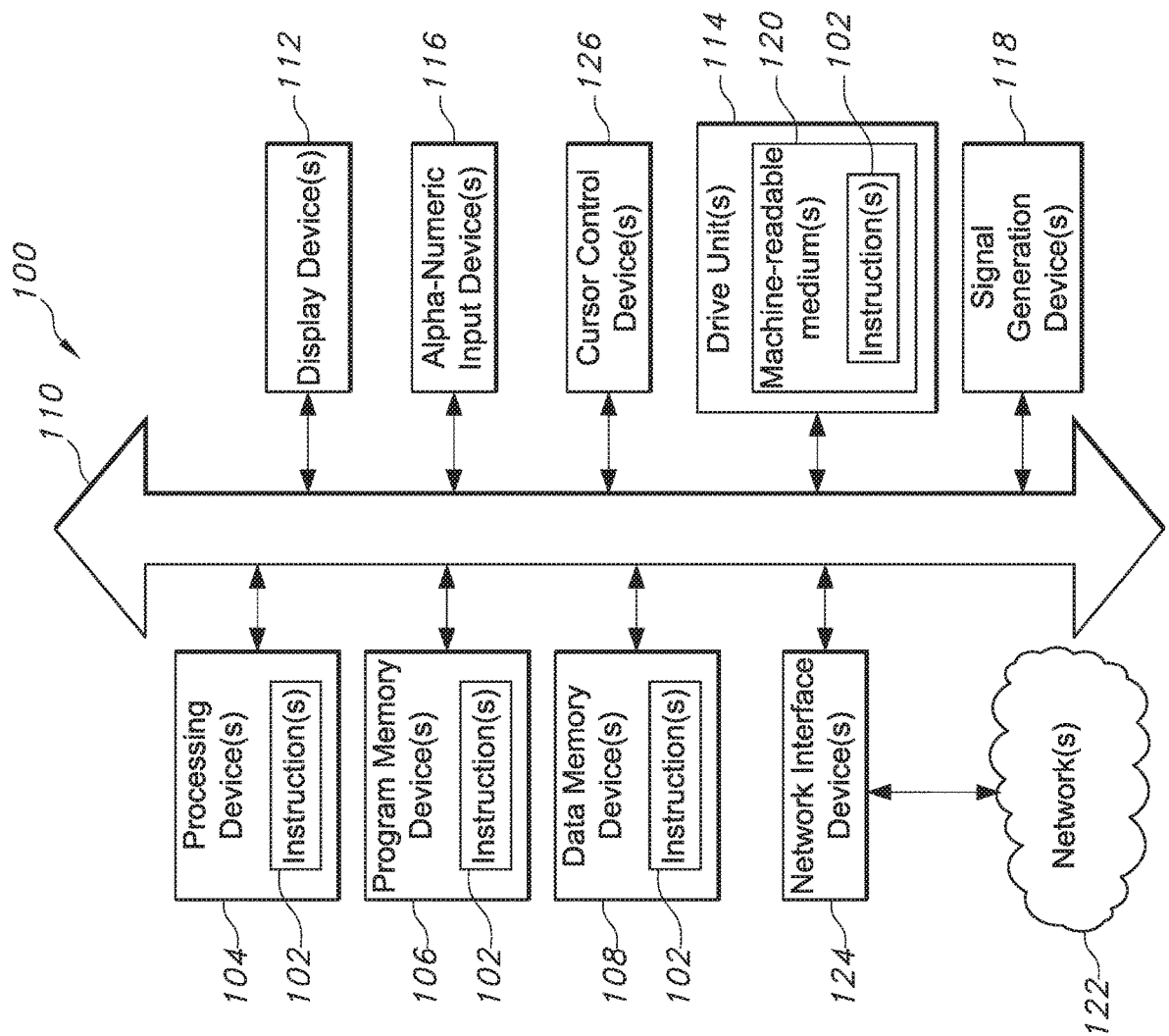
FIG. 7 is a block diagram showing at least a portion of an exemplary machine in the form of a computing system configured to perform methods according to one or more embodiments disclosed herein.

FIG. 7 is a block diagram of an embodiment of a machine in the form of a computing system 100, within which is a set of instructions 102 that, when executed, cause the machine to perform any one or more of the methodologies according to embodiments of the invention. In some embodiments, the machine operates as a standalone device. In some embodiments, the machine is connected (e.g., via a network 122) to other machines. In a networked implementation, the machine operates in the capacity of a server or a client user machine in a server-client user network environment. Exemplary implementations of the machine as contemplated by the invention include, but are not limited to, a server computer, client user computer, personal computer (PC), tablet PC, Personal Digital Assistant (PDA), cellular telephone, mobile device, palmtop computer, laptop computer, desktop computer, communication device, personal trusted device, web appliance, network router, switch or bridge, or any machine capable of executing a set of instructions (sequential or otherwise) that specify actions to be taken by that machine.

The computing system 100 includes a processing device(s) 104 (e.g., a central processing unit (CPU), a graphics processing unit (GPU), or both), program memory device(s) 106, and data memory device(s) 108, which communicate with each other via a bus 110. The computing system 100 further includes display device(s) 112 (e.g., liquid crystals display (LCD), flat panel, solid-state display, or cathode ray tube (CRT)). The computing system 100 includes input device(s) 116 (e.g., a keyboard), cursor control device(s) 126 (e.g., a mouse), disk drive unit(s) 114, signal generation device(s) 120 (e.g., a speaker or remote control), and network interface device(s) 124, operatively coupled together, and/or with other functional blocks, via bus 110.

The disk drive unit(s) 114 includes machine-readable medium(s) 120, on which is stored one or more sets of instructions 102 (e.g., software) embodying any one or more of the methodologies or functions herein, including those methods illustrated herein. The instructions 102 also reside, completely or at least partially, within the program memory device(s) 106, the data memory device(s) 108, and/or the processing device(s) 104 during execution thereof by the computing system 100. The program memory device(s) 106 and the processing device(s) 104 also constitute machine-readable media. Dedicated hardware implementations, such as but not limited to application specific integrated circuits, programmable logic arrays, and other hardware devices can likewise be constructed to implement the methods described herein. Applications that include the apparatus and systems of various embodiments broadly comprise a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments, the methods, functions or logic described herein is implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement the methods, functions or logic described herein.

The embodiment contemplates a machine-readable medium or computer-readable medium containing instructions 102, or that which receives and executes instructions 102 from a propagated signal so that a device connected to a network environment 122 can send or receive voice, video or data, and to communicate over the network 122 using the instructions 102. The instructions 102 are further transmitted or received over the network 122 via the network interface device(s) 124. The machine-readable medium also contains a data structure for storing data useful in providing a functional relationship between the data and a machine or computer in an illustrative embodiment of the systems and methods herein.

While the machine-readable medium 102 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform anyone or more of the methodologies of the embodiment. The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and/or a digital file attachment to e-mail or other self-contained information archive or set of archives is considered a distribution medium equivalent to a tangible storage medium. Accordingly, the embodiment is considered to include anyone or more of a tangible machine-readable medium or a tangible distribution medium, as listed herein and including art-recognized equivalents and successor media, in which the software implementations herein are stored.

It should also be noted that software, which implements the methods, functions or logic herein, are optionally stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. A digital file attachment to e-mail or other self-contained information archive or set of archives is considered a distribution medium equivalent to a tangible storage medium. Accordingly, the disclosure is considered to include a tangible storage medium or distribution medium as listed herein and other equivalents and successor media, in which the software implementations herein are stored.

As previously stated, although the specification describes components and functions implemented in accordance with embodiments of the invention with reference to particular standards and protocols, the embodiments are not limited to such standards and protocols.

The illustrations of embodiments of the invention described herein are intended to provide a general understanding of the structure of the various embodiments, and they are not intended to serve as a complete description of all the elements and features of apparatus and systems that might make use of the structures described herein. Many other embodiments will become apparent to those of skill in the art given the teachings herein. Other embodiments are utilized and derived therefrom, such that structural and logical substitutions and changes are made without departing from the scope of this disclosure. Figures are also merely representational and are not necessarily drawn to scale. Certain proportions thereof may be exaggerated, while others diminished in order to facilitate an explanation of the embodiments of the invention. Accordingly, the specification and drawings are to be regarded in an illustrative rather than a restrictive sense.

Such embodiments of the inventive subject matter are referred to herein, individually and/or collectively, by the term "embodiment" merely for convenience and without intending to voluntarily limit the scope of this application to any single embodiment or inventive concept if more than one is in fact shown. Thus, although specific embodiments have been illustrated and described herein, it should be appreciated that any arrangement calculated to achieve the same purpose are substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single embodiment. Thus the following claims are hereby incorporated into the Detailed Description, with each claim standing on its own as a separate example embodiment.

The Abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single embodiment. Thus the following claims are hereby incorporated into the Detailed Description, with each claim standing on its own as separately claimed subject matter.

Although specific example embodiments have been described, it will be evident that various modifications and changes are made to these embodiments without departing from the broader scope of the inventive subject matter described herein. Accordingly, the specification and drawings are to be regarded in an illustrative rather than a restrictive sense. The accompanying drawings that form a part hereof, show by way of illustration, and without limitation, specific embodiments in which the subject matter are practiced. The embodiments illustrated are described in sufficient detail to enable those skilled in the art to practice the teachings herein. Other embodiments are utilized and derived therefrom, such that structural and logical substitutions and changes are made without departing from the scope of this disclosure.

This Detailed Description, therefore, is not to be taken in a limiting sense, and the scope of various embodiments is defined only by the appended claims, along with the full range of equivalents to which such claims are entitled.

Given the teachings of the invention provided herein, one of ordinary skill in the art will be able to contemplate other implementations and applications of the techniques of the invention. Although illustrative embodiments of the invention have been described herein with reference to the accompanying drawings, it is to be understood that the invention is not limited to those precise embodiments, and that various other changes and modifications are made therein by one skilled in the art without departing from the scope of the appended claims.

What is claimed is:

1. A prescription-based patient treatment system, the system comprising:
   a communications module operatively coupled to a communication network;
   an agreement signification device configured to capture data indicative of a signature of a patient;
   at least one sensor configured to monitor one or more parameters associated with medical equipment for prescribed treatment of a breathing condition of the patient;
   at least one microcontroller coupled with the communications module and the at least one sensor, the microcontroller being configured to:
   obtain, using the agreement signification device and the at least one sensor, information that is input into the microcontroller and is associated with at least one of the patient, the medical equipment, a physician, and an ancillary provider, the information comprising an agreement by the patient verifying an accuracy of data entered into the patient treatment system by the physician comprising at least one of (i) whether the patient is benefitting from use of the medical equipment, (ii) whether continued use of the medical equipment by the patient is required, (iii) hours of operation of the medical equipment, and (iv) a measure of efficacy of the prescribed treatment;
   convert the information into a digital format enabling verification that the information complies with a prescription for a prescribed treatment associated with the medical equipment;
   transmit to a remote user, via the communications module, data indicative of real-time status and usage of the medical equipment by the patient, wherein the data includes an apnea hypopnea index (AHI) associated with a severity of the breathing condition of the patient calculated by the medical equipment;
   generate at least one signal causing the medical equipment to automatically administer or discontinue administration of the prescribed treatment using the medical equipment, as a function of the information; and
   receive, from the remote user over the communication network, at least one control signal generated by the remote user to modify the prescription for the prescribed treatment to a modified prescription prescribed by the physician based on the real-time status and usage of the medical equipment including the AHI associated with the severity of the breathing condition of the patient, the microcontroller automatically adjusting an amount and/or frequency of at least one parameter of the medical equipment being currently prescribed for administration to the patient from a first in-use value to a second value as a function of the at least one control signal to thereby change an operation of the medical equipment in accordance with the modified prescription for the prescribed treatment, wherein the prescribed treatment using the medical equipment facilitates identification of the severity of the breathing condition and treatment of the patient based at least on the severity of the breathing condition in accordance with the modified prescription without a need for an in-office doctor-patient visit.

2. The system of claim 1, wherein the microcontroller is further configured to provide selective access to the information in the patient treatment system, the access being selectively provided in real-time to at least one of the physician, the ancillary provider, a payor, and an auditor.

3. The system of claim 1, wherein the at least one parameter of the medical equipment comprises at least one of airway pressure, air, oxygen, transcutaneous electrical nerve stimulation, continuous passive motion, mobility assistance, parenteral nutrition, enteral nutrition, and dialysis to the patient.

4. The system of claim 1, wherein the medical equipment comprises at least one of an airway pressure device, a ventilator, an oxygen delivery device, a parenteral nutrition device, an enteral nutrition device, and a dialysis device.

5. The system of claim 1, further comprising a global positioning system (GPS) device coupled to the microcontroller and configured to capture latitude and longitude coordinates of the medical equipment, the microcontroller being configured to transmit the latitude and longitude of the medical equipment to a remote user over the communication network for verifying a location of the medical equipment.

6. The system of claim 1, wherein the at least one sensor and the at least one microcontroller are integrated within the medical equipment.

7. The system of claim 1, further comprising an interface circuit coupled between the at least one sensor and the microcontroller, the interface circuit comprising signal conditioning circuitry configured to receive one or more signals from the at least one sensor and to generate one or more corresponding output signals in a form compatible with the microcontroller.

8. The system of claim 7, wherein the signal conditioning circuitry comprises at least one of an amplifier, filter, analog-to-digital converter, digital-to-analog converter, voltage translator and voltage level shifter.

9. The system of claim 1, wherein the communications module comprises:
a transmitter, the transmitter being configured to send, to a remote user over the communication network, data generated by the microcontroller and/or stored in a memory of the patient treatment system that is indicative of at least one of an operation and a status of the medical equipment; and
a receiver, the receiver being configured to receive data supplied to the patient treatment system for at least one of requesting the patient treatment system to send information regarding the status and/or operation of the medical equipment, and controlling an operational parameter of the medical equipment by the remote user.

10. The system of claim 1, further comprising a memory coupled with the at least one microcontroller, the memory storing historical data relating to at least one of an operational status of the medical equipment, patient physiological information, and patient usage information corresponding to the medical equipment.

11. The system of claim 1, wherein the microcontroller and the at least one sensor are connected together in a closed-loop feedback arrangement to control one or more parameters of the medical equipment as a function of data generated by the at least one sensor, whereby treatment of the patient by the medical equipment is maintained within prescribed parameters.

12. The system of claim 1, wherein the microcontroller is further configured to obtain a user identifier associated with the medical equipment using a feature of the communications module without user intervention, the user identifier representing an identity of an ancillary company technician scanning the medical equipment.

13. The system of claim 1, wherein the information comprises ancillary provider information, the ancillary provider information comprising at least one of an image or video of an hours-of-operation display of the medical equipment, functional information associated with diagnostic testing, whether the patient has had any problems with the medical equipment, whether the patient is benefitting from the medical equipment, whether the patient needs to continue using the medical equipment, whether the patient is non-compliant with the prescribed usage of the medical equipment yet has been instructed to use the medical equipment correctly, and in-home diagnostic testing and gathering information requested by the physician comprising at least one of blood gasses, international normalized ratio (INR) Coumadin® testing, apnea hypoxia index (AHI), ventilators, spirometry, and pulse oximetry.

14. The system of claim 1, wherein the communications module is wirelessly coupled to the communication network.

15. A prescription-based method for use in conjunction with a patient treatment system for remotely verifying, in real time, compliance of prescribed treatment of a of a breathing condition of a patient using medical equipment, the patient treatment system including a communications module operatively coupled to a communication network, an agreement signification device configured to capture data indicative of a signature of the patient, at least one sensor configured to monitor one or more parameters associated with the medical equipment for the prescribed treatment of the breathing condition of the patient, and at least one microcontroller coupled with the communications module and the at least one sensor, the method comprising:
obtaining information entered into the patient treatment system, the information being associated with at least one of the patient, the medical equipment, a physician, and an ancillary provider, the information comprising an agreement by the patient verifying an accuracy of data entered into the patient treatment system by the physician, including at least one of (i) whether the patient is benefitting from use of the DME, (ii) whether continued use of the DME by the patient is required, (iii) the hours of operation of the DME, and (iv) a measure of the efficacy of the prescribed treatment;
converting the information into a digital format to enable verification that the information regarding patient medical equipment usage complies with a prescription for a prescribed treatment associated with the medical equipment;
transmitting to a remote user, via the communications module, data indicative of real-time status and usage of the medical equipment to a remote user by the patient, wherein the data includes an apnea hypopnea index (AHI) associated with a severity of the breathing condition of the patient calculated by the medical equipment;

generating, using the at least one microcontroller, at least one signal causing the medical equipment to automatically administer or discontinue administration of the prescribed treatment using the medical equipment, as a function of the information; and receiving, from the remote user over the communication network, at least one control signal generated by the remote user to modify the prescription for the prescribed treatment to a modified prescription prescribed by the physician based on the real-time status and usage of the medical equipment including the AHI associated with the severity of the breathing condition of the patient, the microcontroller automatically adjusting an amount and/or frequency of at least one parameter of the medical equipment being prescribed for administration to the patient from a first in-use value to a second value as a function of the at least one control signal to thereby change an operation of the medical equipment in accordance with the modified prescription for the prescribed treatment, wherein the prescribed treatment using the medical equipment facilitates identification of the severity of the breathing condition and treatment of the patient based at least on the severity of the breathing condition in accordance with the modified prescription without a need for an in-office doctor-patient visit.

16. The method of claim 15, further comprising providing selective access to the information in the patient treatment system, the access being selectively provided in real-time to at least one of the physician, the ancillary provider, a payor, and an auditor.

17. The method of claim 15, further comprising:
automatically capturing, by the microcontroller, latitude and longitude coordinates of the medical equipment; and
transmitting, by the communications module, the latitude and longitude coordinates of the medical equipment to a remote user over the communication network for verifying a location of the medical equipment.

18. The method of claim 15, wherein the at least one parameter of the medical equipment comprises at least one of airway pressure, air, oxygen, transcutaneous electrical nerve stimulation, continuous passive motion, mobility assistance, parenteral nutrition, enteral nutrition and dialysis to the patient.

* * * * *